United States Patent
Lee et al.

(10) Patent No.: US 10,386,364 B2
(45) Date of Patent: Aug. 20, 2019

(54) MAGNETIC BEAD AGGREGATION ASSAY SYSTEM

(75) Inventors: Gil Lee, Dublin (IE); Peng Li, Dublin (IE); Mark Platt, Loughborough (GB); Gemma Cannon, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 794 days.

(21) Appl. No.: 14/131,328

(22) PCT Filed: Jul. 9, 2012

(86) PCT No.: PCT/EP2012/063440
§ 371 (c)(1),
(2), (4) Date: Mar. 26, 2014

(87) PCT Pub. No.: WO2013/004852
PCT Pub. Date: Jan. 10, 2013

(65) Prior Publication Data
US 2014/0227679 A1 Aug. 14, 2014

(30) Foreign Application Priority Data

Jul. 7, 2011 (EP) .................. PCT/EP2011/061550
Dec. 6, 2011 (GB) ................................... 1120965.7

(51) Int. Cl.
*G01N 33/50* (2006.01)
*G01N 33/543* (2006.01)
*B03C 1/01* (2006.01)
*B03C 1/28* (2006.01)

(52) U.S. Cl.
CPC ......... *G01N 33/54326* (2013.01); *B03C 1/01* (2013.01); *B03C 1/288* (2013.01); *B03C 2201/18* (2013.01); *B03C 2201/24* (2013.01); *B03C 2201/26* (2013.01); *G01N 2446/84* (2013.01)

(58) Field of Classification Search
CPC .......... G01N 33/54326; G01N 2446/84; B03C 1/01; B03C 1/288; B03C 2201/18; B03C 2201/24; B03C 2201/26
See application file for complete search history.

(56) References Cited

U.S. PATENT DOCUMENTS

| | | | |
|---|---|---|---|
| 5,681,478 A | 10/1997 | Lea et al. | |
| 6,620,627 B1 * | 9/2003 | Liberti | G01N 33/54326 422/533 |
| 7,232,691 B2 * | 6/2007 | Kraus, Jr. | B03C 1/00 422/186 |
| 2002/0034790 A1 * | 3/2002 | Li | C07H 21/00 435/91.1 |
| 2003/0170686 A1 | 9/2003 | Hoet et al. | |
| 2004/0106157 A1 * | 6/2004 | Nakahara | G01N 33/535 435/7.4 |
| 2006/0216239 A1 * | 9/2006 | Zhang | A61K 49/1845 424/9.34 |
| 2008/0309335 A1 * | 12/2008 | Paxon | G01N 21/6428 324/309 |
| 2010/0291219 A1 * | 11/2010 | Karp | A61K 35/32 424/489 |
| 2010/0304368 A1 * | 12/2010 | Cherkasov | C07H 19/10 435/6.1 |
| 2012/0077284 A1 * | 3/2012 | Soldo | G01N 33/543 436/501 |
| 2012/0187938 A1 | 7/2012 | Bär et al. | |

FOREIGN PATENT DOCUMENTS

WO 2011020011 A2 2/2011

OTHER PUBLICATIONS

Nagasaki et al., Enhanced immunoresponse of antibody/mixed-PEG co-immobilized surface construction of high-performance immunomagnetic ELISA system, Journal of Colloid and Interface Science 309, 2007, pp. 524-530.*
International Searching Authority, U.S. Patent and Trademark Office; International Preliminary Report on Patentability for PCT/EP2012/063440; dated Oct. 2, 2014; 16 pages.

* cited by examiner

*Primary Examiner* — Gary Counts
(74) *Attorney, Agent, or Firm* — Holzer Patel Drennan

(57) ABSTRACT

There is provided a method of aggregating a plurality of beads in a magnetic bead aggregation assay for subsequent analysis comprising: —providing magnetic beads comprising a capture probe for binding with said target analyte; —reacting the magnetic beads with the sample including a target analyte in a reaction chamber aggregating the magnetic beads in the presence of a magnetic field with the target analyte to allow formation of magnetic bead aggregates having physical properties detectable to enable characterization of the aggregates on an aggregate by aggregate basis using a detector to measure the physical properties of the aggregates. Further provided are a method and system for detecting analytes in a sample by characterizing the magnetic bead aggregates on an aggregate by aggregate basis by measuring physical properties of the aggregates.

15 Claims, 25 Drawing Sheets

Example 2: Separation of rare cell-virus-protein for diagnostics by using double magnetic beads

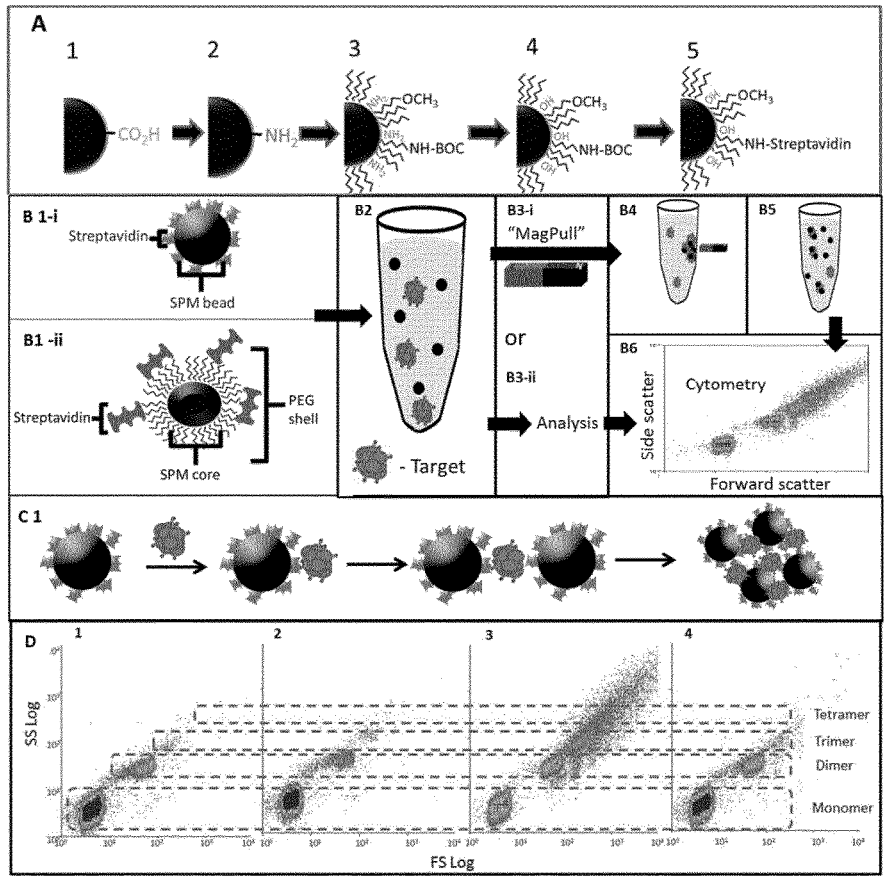

Figure 4A to 4D. Schematic of MBA-FC assay based Schematic of a magnetic bead agglutination– flow cytometry based assay. Figure 4A illustrates capture of analyte and aggregation of superparamagnetic materials (SPMs) beads using MBA. Figure 4B1 SPM's were either (i) purchased with a streptavidin monolayer or (ii) carboxyl beads were coated with PEG and conjugated to an antibody of choice. Figure 4B2 SPM's were incubated with target. 4B3i Aggregation of the beads was aided by the use of a magnetic field. Figure 4B3-ii Samples can aso be analysed without MBA. Figure 4B4/B5 Using the magpull strategy the beads may be washed and resuspended before analysis. Figure 4B6 The aggregation state of the SPMs was determined using flow cytometry; showing additionally. Figure 4C Schematic of analyte and aggregations of SPMs using MBA and Figure 4D FC analysis of assays executed using 50 fM of 3 μm streptavidin beads, shown in B1-i, with a binding capacity 75 nM, 30 min reaction time. BBSA at concentrations of 1) $3 \times 10^{-4}$ nM, 2) 0.03 nM, 3) 3 nM, and 4) 300 nM.

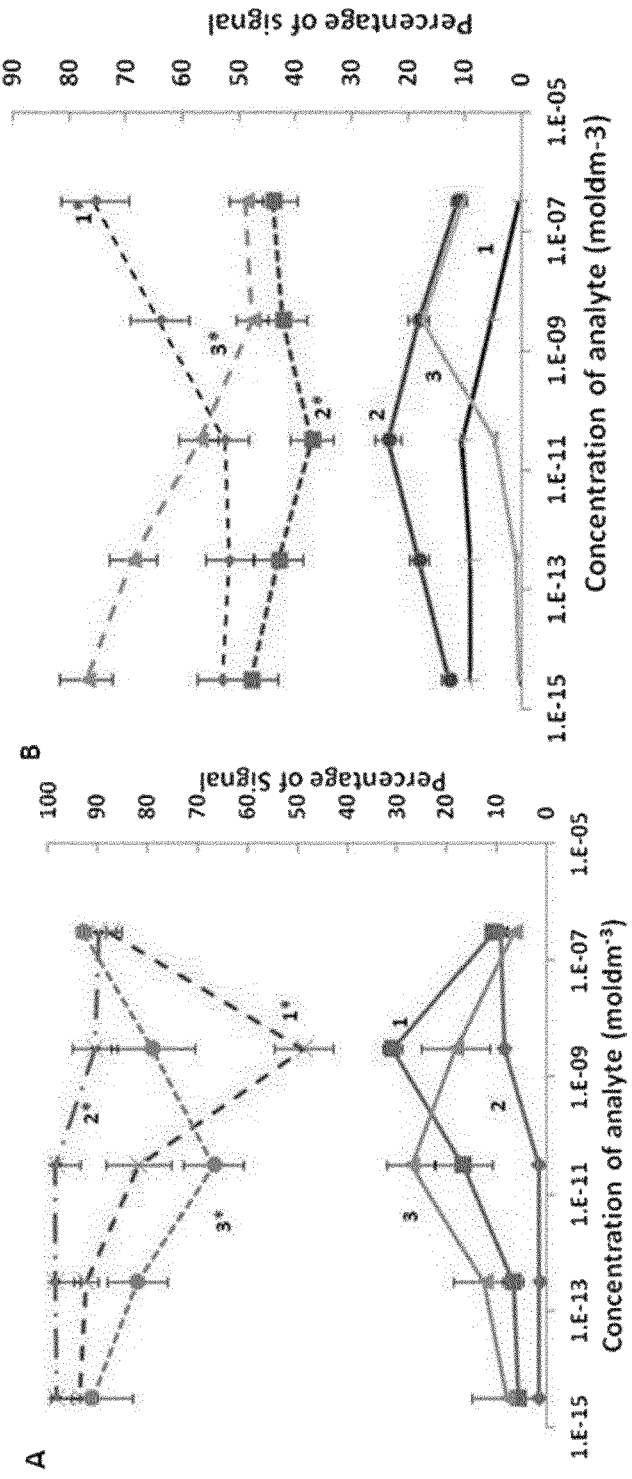

Figures 7. Influence of bead properties on the response of the biotin-streptavidin MBA-FC assay. A Distribution of 3 μm bead monomers (denoted with *) and dimers as the bead concentration and binding capacity are varied. Curves 1 and 1* - 50 fM bead concentration, 75 nM binding capacity. Curves 2 and 2* - 50 fM bead concentration, binding capacity of 8 nM. Curves 3 and 3* - 5 fM bead concentration, binding capacity of 7 nM. B Formation of 1 μm bead monomers (denoted *) and tetramers as the bead concentration and binding capacity of the beads are varied. Curve 1 and 1* - 5 fM bead concentration, binding capacity 0.52 nM. Curves 2 and 2* - 50 fM bead concentration, binding capacity 5.2 nM. Curves 3 and 3* - 500 fM bead concentration, binding capacity 52 nM  These reactions were carried out in PBST buffer for 30 mins followed by magpull and FC analysis. Blank assays were found to have a aggregation levels below 3±2% in all assays in this study.

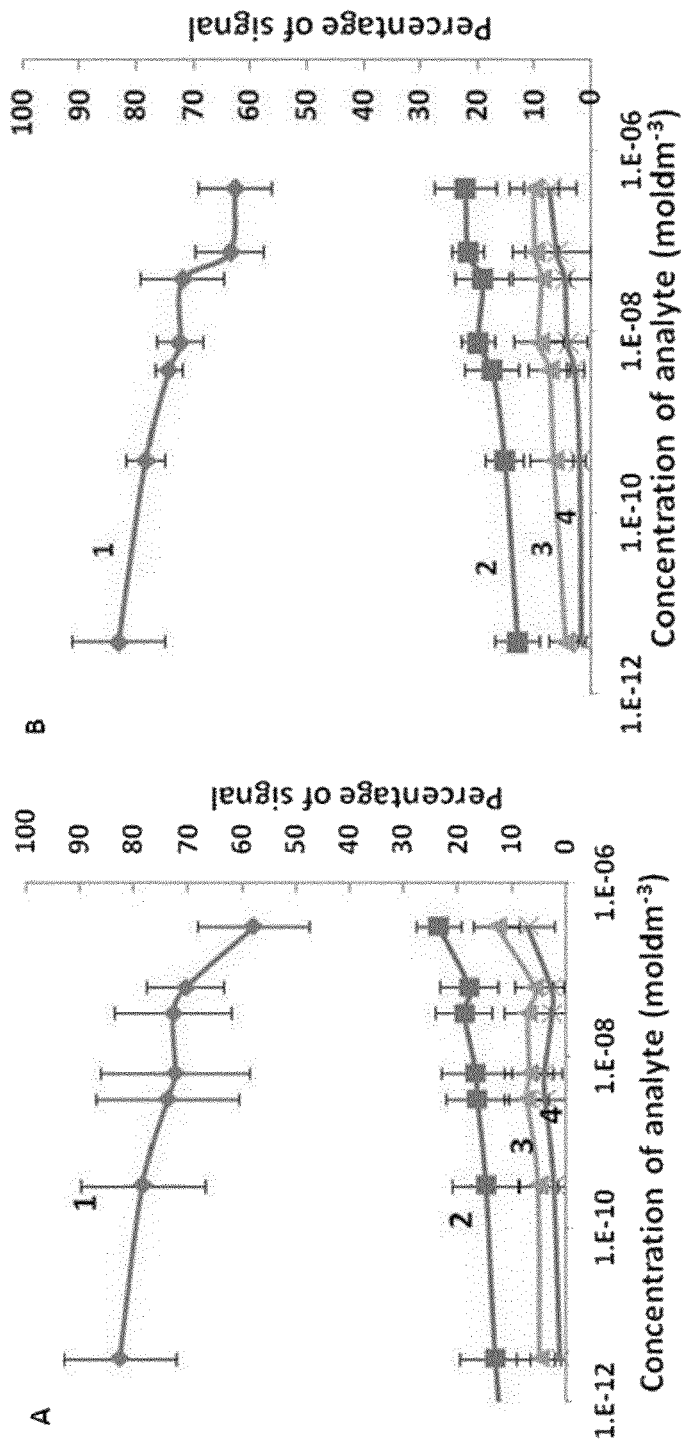

Figure 8. HSV-1 and 2 MBA-FC assay - Curve 1 – monomers, 2 – dimers, 3 – trimers and 4 – tetramers of SPMs. A Formation of aggregates of 3 μm SPMs as a function of HSV-2 antigen concentration in PBST, 50 fM bead concentration, binding capacity of 3 nM. B Formation of aggregates of 1 μm SPMs as a function of HSV-1 antigen concentration in PBST, 500 fM bead concentration, binding capacity of 3 nM. In each assay the SPMs were reacted with the analytes for 30 mins in PBST. Blank assays were found to have a aggregation level below 3±2%.

*Zeta potential for beads used in the assays.*

*SEM images SPB's. (left) Invitrogen m270, (right) Invitrogen Myone.. Scale bar in is equal to one micron.*

*Flow cytometry data for 1μm streptavidin beads- 30 min assay, Percentage of aggregates of beads as a function of analyte concentration. Bead concentration of 500 fM bead concentration. 30 min assay A- with magpull, B – no magpull.*

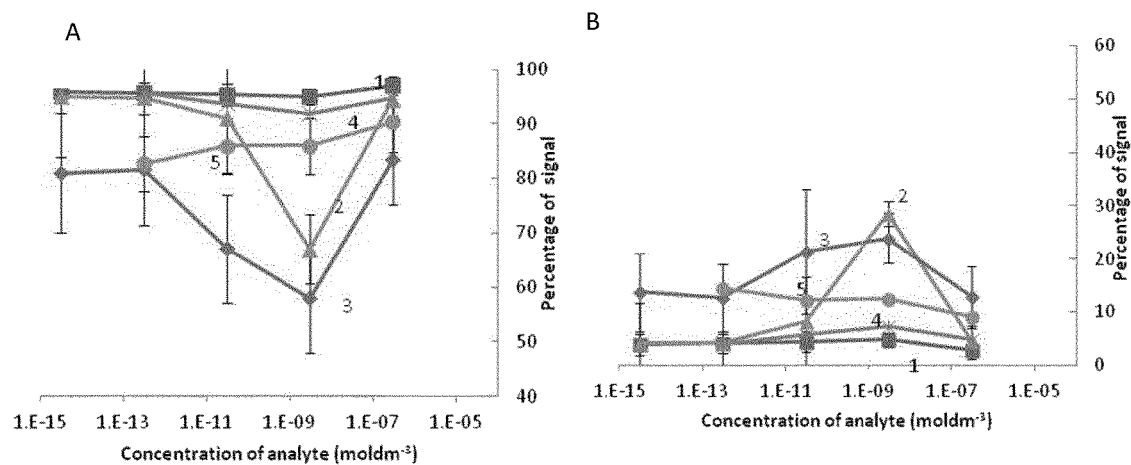

*Figure 13*

*PEG modified 3 micron beads, 50fM - number of monomers(A) and dimers (B) in sample after assay time 30 mins, (with magpull). Curves 1, 2 and 3, PEG modified beads coated with Streptavidin binding capacity 1 = 1 nM, 2 = 7 nM, 3 = 12 nM, assay ran in PBST. Curves 4 and 5 were ran in BSA spiked FSA samples for 30 mins, 4 PEG modified bead with a binding capacity of 7nM, 5 commercial unmodified streptavidin bead, binding capacity 70 nM.*

*Relative fraction of monomers for HSV-2 assay using 3 micron PEG modified beads, assay time 30 mins. 1-Polyclonal antibodies, with magpull. 2-Monoclonal antibody modified beads, with magpull. 3-Monoclonal antibody modified beads without magpull.*

Cytometry scatter plots for "Blank" samples. A) 3 μm Streptavidin beads direct from supplier, R2 contains the data from nonspecific aggregation, 8% of the population. B) 3 μm PEG modified Streptavidin beads, R2 contains the data from nonspecific aggregation, 3% of the population. C) 1 μm commercial Streptavidin beads.

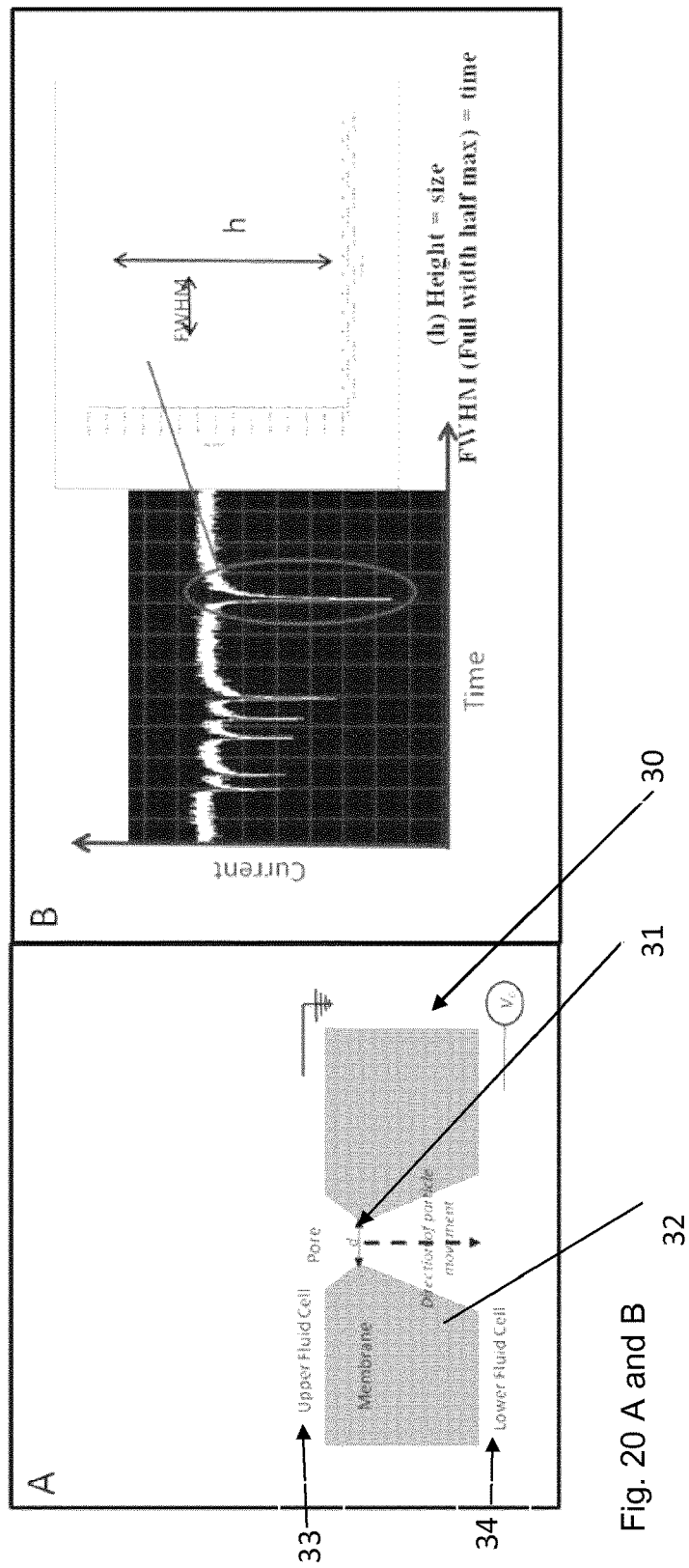
Fig. 20 A and B

Figure 22A Height (nA) versus % population. Insert – average size (y axis) over the course of the experiment in seconds (x axis). Figure 22B FWHM (ms) verus % population;

i = 1 micron sphere ii = 4.7 micron long rod iii = 2 micron long rod

MAGNETIC BEAD AGGREGATION ASSAY SYSTEM

PRIORITY CLAIM

The present application is an U.S. 371 National Phase Patent Application and claims benefit of Patent Cooperation Treaty application No. PCT/EP2012/063440, entitled "Magnetic Bead Aggregation Assay System and Method for Analysing and Charaterising Magnetic Bead Aggregation and Detection of Target Analytes" and filed on 9 Jul. 2012, which takes priority from European Patent Application No. PCT/EP2011/061550 filed on 7 Jul. 2011 and U.K. Patent Application 112096.7 filed on 6 Dec. 2011, all of which are incorporated herein by reference in their entirety.

FIELD

The present invention relates to magnetic bead aggregation assays and a system and method for the characterization of the aggregation assay and detection of target analytes.

BACKGROUND

Bio-separation describes techniques used for determining the molecular state of a cell, or whole organism. Currently, bio-separation is often performed using liquid chromatography, electrophoresis or centrifugation, which achieves separation by transporting an analyte relative to a stationary phase based on a physical or chemical property, such as surface chemistry, size, charge, or mass density. Although these techniques are able to separate analytes with a high resolution they are slow and often difficult to implement. For example, when screening for sexually transmitted infections (STIs) rapid diagnosis is critical as delays can lead to progression of chronic disease, infertility, cancer, and contribute to continued pathogen and disease transmission. Point of care testing for some STIs can often be difficult as antigens are often present at levels below the current sensitivity of point of care testing technologies, and samples can often require pre-treatment involving purification or filtration. This ultimately leads to an analysis time that takes longer than is acceptable. Assays that measure fluorescence or light scattering have been provided. To operate such an assay it is typically necessary that the assay beads be functionalized with additional materials to provide a basis for measurement. Such systems do not have the capacity to provide a quantitative measurement of specific particles. Typically such systems are directed to providing only an indication that a specific particle is present. Techniques such as light scattering respond non-linearly to different size particles. It is not possible to use such approaches to count individual particles. Other aggregation assay methods have relied upon two main modes of detection—monitoring the aggregation as a function of analyte concentration measuring chain length or turbidity, monitoring a change in magnetic properties as particles are forced to be in close proximity to each other. Such techniques have a limited dynamic range and are difficult to multiplex. In biosensing there is a need for improved detection systems that operate with short analysis time and provide improved accuracy of measurement of analytes. There is further a need for improved point of care testing systems that are robust and easy to operate.

There is therefore a need to address these and other problems and limitations of prior art separation devices and methods. There is a need to for a more efficient and reliable and sensitive assay method and approach that addresses the above noted problems.

SUMMARY

According to a first aspect, the present specification there is provided a method of aggregating a plurality of beads for subsequent analysis comprising:
Providing a container with a sample solution with beads in the presence of a magnetic field of a first orientation;
Allowing the beads to migrate to and collect on a side surface of the container;
Exposing the beads to a magnetic field of a second orientation to allow formation of aggregates of the beads.

The may comprise subsequent to the collection of the beads on a side surface of the container, replacing the sample solution with a second solution and re-exposing the new solution to a magnetic field to allow the beads to migrate to and collect on the side surface of the container. The method may comprise prior to exposing the beds to the magnetic field, incubating the beads with a target analyte. The beads may be magnetic beads.

According to a second aspect, the present specification provides a method of aggregating a plurality of beads in a magnetic bead aggregation assay for subsequent analysis comprising:
providing magnetic beads comprising a capture probe for binding with said target analyte;
reacting the magnetic beads with the sample including a target analyte in a reaction chamber aggregating the magnetic beads in the presence of a magnetic field with the target analyte to allow formation of magnetic bead aggregates having physical properties detectable to enable characterisation of the aggregates on an aggregate by aggregate basis using a detector to measure the physical properties of the aggregates.

In the methods of the first and second aspects, the beads may be super-paramagnetic beads. The physical properties may be predefined physical properties. The method may further comprise providing magnetic beads of a first type comprising a capture probe for binding with a first analyte and providing magnetic beads of a second type comprising a capture probe for binding with a second analyte to form aggregates of the first and second magnetic beads having predefined physical properties detectable to enable characterisation of the aggregates of the first and second magnetic beads on a bead by bead basis using a detector to measure the physical properties of the aggregates to detect first and second analytes. The beads of a first type or second type are preferably uniform in physical properties, i.e., magnetization, color and size The magnetic particles may comprise carboxyl coated particles. The particles may be modified with a protective layer. The particles may be modified with a protective PEG layer. The magnetic particles may be provided with a protein coating. The protein coated magnetic particle may be coupled to a biotinylated nucleic acid probe. The protein may be streptavidin.

The aggregation of magnetic beads to form aggregates is controllable by controlling bead concentration. The aggregation of magnetic beads to form aggregates is controllable by controlling binding capacity. The magnetic beads are reacted with the sample for a reaction time and wherein aggregation of magnetic beads to form aggregates is controllable by controlling reaction time. An increased reaction time provides an increase in the aggregation rate.

The method further comprising the step of applying a magnetic force to provide the magnetic field for aggregating the magnetic particles wherein the aggregation of magnetic particles to form aggregates is controllable by controlling application of magnetic force. The application of a magnetic force provides an increase in particle-particle interactions and an increase the number of particle aggregates. The magnetic field comprises a magnetic gradient or a time varying magnetic field.

The step of applying a magnetic force preferably comprises
  applying a magnetic field of a first orientation to the reaction chamber containing magnetic particles and the sample solution;
  allowing the magnetic particles to migrate to and collect on a side surface of the container;
  exposing the magnetic particles to a magnetic field of a second orientation to promote formation of aggregates of the magnetic particles.

The aggregation of magnetic beads to form aggregates is controllable by controlling magnetic bead size. The rate of aggregation of the magnetic beads increases with a decrease in magnetic particle size. The beads are selected from beads having a size range of the order of 10 nm to 10,000 nm diameter. The beads are preferably in the range of 0.1-5 micron diameter, most preferably 0.2 to 2 microns. The rate of aggregation of the magnetic beads to form aggregates further increases with an increase in the density of the magnetic beads. The rate of aggregation of the magnetic beads to form aggregates further increases with an increase in the density of the magnetic beads. The rate of aggregation of the magnetic beads to form aggregates further increases with an increase in the concentration of the analyte in the sample solution. The rate of aggregation of the magnetic beads to form aggregates further increases with the affinity of the capture probe with the target analyte. The method wherein magnetic bead size and/or binding capacity and/or avidity/affinity and particle concentration are controllable to control sensitivity of the assay The method wherein magnetic particle size and/or binding capacity and/or avidity/affinity and particle concentration are controlled taking account of the onset of the hook effect for the magnetic particle aggregation assay.

According to a third aspect, the present specification provides a magnetic bead aggregate formed by the method of the first and second aspects. The magnetic bead aggregate may be a monomer or dimer or trimer or tetramer. An aggregate of one or more magnetic beads with an analyte have predefined physical properties.

According to a fourth aspect, the present specification provides a magnetic particle complex comprising:
  A first magnetic particle coupled to a nucleic acid probe; and
  A second magnetic or fluorescent particle coupled to a nucleic acid probe.

The first magnetic particle and the second magnetic or fluorescent particle may be coupled to the same nucleic acid probe. Preferably, the magnetic particles are covalently coupled to the nucleic acid probe. The magnetic particle complex may comprise a complex wherein:
the nucleic acid probes are DNA or RNA; and/or
the nucleic acid probes contain degenerate bases; and/or
the nucleic acid probes are of varying length; and/or
the nucleic acid probe contain a ligand complementary to the surface of the magnetic or fluorescent particles.

The first magnetic particle may be provided with a protein coating. The protein coated first magnetic particle may be coupled to a biotinylated nucleic acid probe. The protein is preferably streptavidin.

According to a fourth aspect, the specification provides a method of characterising an aggregation of magnetic beads as described or as produced by the aggregation method of the first and second aspects in a magnetic bead aggregation assay comprising:
  providing magnetic bead aggregates to a detector configured to characterise the magnetic bead aggregates
  characterising the magnetic bead aggregates on an aggregate by aggregate basis, wherein the characterization of the magnetic bead aggregation is based on measuring physical properties of said magnetic bead aggregates.

According to a fifth aspect there is provided a method of characterising an aggregation of magnetic beads in a magnetic bead aggregation assay, the method comprising
  providing magnetic particles configured to bind with a target analyte in an assay
  reacting the magnetic beads in a reaction chamber with a sample containing the target analyte
  aggregating the magnetic beads in the presence of a magnetic field with the target analyte to form magnetic bead aggregates
  analysing magnetic bead aggregates in a detector configured to characterise the magnetic bead aggregates
  characterising the magnetic bead aggregates on an aggregate by aggregate basis, wherein the characterization of the magnetic bead aggregation is based on measuring physical properties of said magnetic bead aggregates.

The aggregates of one or more magnetic beads with an analyte preferably have predefined physical properties. The characterization of the magnetic bead aggregates is based on measuring physical properties of the aggregates on an aggregate by aggregate basis.

The characterization of the magnetic bead aggregates may be based on measuring magnetic moment of the aggregates/particles. The characterization of the magnetic bead aggregates may be based on measuring volume of the aggregates. The characterization of the magnetic bead aggregates may be based on measuring size of the aggregates.

The method may comprise analysing the magnetic bead aggregates using an optical detection means to characterize the aggregates based on measuring the volume of the aggregates. The optical detection means may be a flow cytometer. The method may include analysing the magnetic bead aggregates using an NLM means to characterize the aggregates based on measuring the magnetic moment and/or volume of the aggregates. The characterisation of the aggregates on an aggregate by aggregate basis enables identification of the aggregates and analytes in a sample. The method may include providing the magnetic bead aggregate to a F-NLM detector to characterize the aggregation based on measuring the magnetic moment of the aggregates and/or volume of the aggregates. The beads are preferably superparamagnetic beads. The magnetic bead aggregates may be monomers and/or dimers and/or trimers and/or tetramers.

The step of aggregating the beads in a magnetic field further may comprise applying an external magnetic field to the magnetic beads to promote aggregation of the magnetic beads to form aggregates. The magnetic field may be a magnetic field gradient. The magnetic field is a travelling magnetic field. The method may include the step of transporting the magnetic bead aggregates from the reaction chamber to the detection means for detection. Detecting the aggregates on an aggregate by aggregate basis may comprise the further steps of: releasing the external magnetic field applied for the aggregating step and isolating the aggregates by transporting the aggregates to the detector for sensing.

The detection means may be an optical detection system and the method may comprise isolating the aggregates by transporting them to chambers for sensing. The transporting may be by injecting the sample into a flow stream. The transporting may be by flow from the reaction chamber. The transporting may be by hydrodynamic flow. The transporting may be by gravity. The flow stream preferably focuses the aggregates.

The detection means may be an optical detection means. The optical detection means comprises a flow cytometer. The optical detection means is preferably configured to identify in the range of 1000 to 100,000 particle aggregates/min, preferably 10,000 to 100,000 particle aggregates/min.

The detection means comprises a pore detection means. And the transporting may comprise forcing the aggregates 155 through a pore or a number of parallel pores.

The detection means comprises NLM chip and the aggregates are detected on the chip. The application of the local magnetic field preferably allowing the particle aggregates to be sensed on individual micromagnets. The aggregates are preferably detected on the chip using an optical detector or magnetometer.

The analysing means may comprise an F-NLM separator for separating the aggregates in series with a detection means for example an optical detection means.

The NLM detection means is preferably configured to identify of the order of 1000-1,000,000 individual particle aggregates on a large micro-magnet array, preferably 10,000 to 100,000.

The sensitivity of the assay system preferably increases with the density and affinity of the receptors on the beads, which is attributed to an increase in the rate of accumulation of the analyte on the beads. The characterisation of the aggregates on an aggregate by aggregate basis enables identification of the aggregates in a sample. The characterisation of the aggregates on a particle by particle basis enables identification of analytes in a sample.

According to a sixth aspect, there is provided a magnetic bead aggregation system for the detection of an analyte in a sample by magnetic bead aggregation, the system comprising
  a reaction chamber in which a sample is reacted with magnetic beads
  an aggregating means for promoting formation of aggregates, and
  an analysing means for analysing and characterizing aggregates in said sample on an aggregate by aggregate basis.

The analysing means may comprise an optical detection means. The analysing means comprises a flow cytometer. The analysing means comprises an NLM detector. The analysing means comprises a particle size detector. The analysing means is configured to characterize the magnetic particle aggregates based on measuring physical properties of said magnetic particle aggregates, on an aggregate by aggregate basis. Said physical properties may be magnetic moment, and/or volume. The aggregating means preferably comprises a magnetic means for applying a magnetic field to promote aggregation.

The analysing means may comprise an NLM detector. The aggregates may be detected on the chip.

The analysing means comprises an F-NLM separator for separating the aggregates and a detection means for example an optical detection means for detecting said aggregates.

Characterisation of the aggregates on an aggregate by aggregate basis enables identification of the aggregates in a sample. Characterisation of the aggregates on a particle by particle basis enables identification of analytes in a sample.

The aggregating means preferably comprises magnetic means.

The system may further comprise transport means for transporting magnetic particle aggregates from the reaction chamber to the analysing means. The transport means may be flow.

According to a seventh aspect there is provided a device or kit for the determination, by magnetic particle agglutination, the presence of an analyte in a sample, characterized in that it includes:
a) a reaction chamber for reacting a sample containing a target analyte with the magnetic particles to form a magnetic particle agglutinate, the magnetic particles comprising a capture probe for capturing a target analyte to form an agglutinate,
b) a detector configured to characterize the magnetic particle agglutinate based on measuring physical properties of said magnetic particle agglutinate.

The physical properties preferably being magnetic moment and/or volume.

According to an eighth aspect there is provided a method for detecting an analyte in a sample, the method comprising
  contacting the analyte in a sample with magnetic particles comprising a capture probe for capturing said analyte, the capture probe being configured to act as a centre for controlled aggregation of magnetic particles with said analyte to form an aggregate of predefined form,
  detecting the analyte by detecting physical properties of the aggregate.

The particles preferably comprise superparamagnetic beads. The method may be applied to detecting physical properties of aggregates formed by the method of the first or second aspects and to aggregates or complexes of the third and fourth aspects.

According to a still further aspect of the present specification there is provided a method for detecting an analyte in a sample, the method comprising contacting the analyte in a sample with nanoparticles comprising a capture probe for capturing said analyte, the capture probe being configured to act as a centre for controlled aggregation of nanoparticles with said analyte to form an aggregate of predefined form, detecting the analyte by detecting the shape and/or size of the aggregate.

In one embodiment, the nanoparticles comprise rod shaped particles. In another embodiment the nanoparticles comprise an aspect ratio greater than 1. In one embodiment, detecting the analyte comprises detecting the change in shape and/or size of the particles in the sample resulting from the aggregation with the analyte. The aggregate may have a predefined shape. The aggregate may have a predefined size. In one arrangement the nanoparticles may be configured to aggregate end to end with an analyte to form an aggregate of detectably increased length. In another arrangement the nanoparticles may be configured to aggregate side by side with an analyte to form an aggregate of detectably increased size or width. The location of the capture probe on the nanoparticle may be varied as required to control aggregation and the form of the resulting aggregate. Detecting an analyte may comprise detecting the size of aggregates passing through a detector. Detecting an analyte may comprise detecting the shape of aggregates passing through a detector.

Detecting an analyte may comprise detecting the full width half maximum (FWHM) signal, the signal being indicative of the time taken for the particle or aggregate to traverse the detector. The full width half maximum (FWHM) signal providing an indication of particle or aggregate length. Detecting an analyte may comprises detecting the change in base line current $\Delta$ip signal, the signal being indicative of the blockade event. The percentage (%) change in the base line current $\Delta$ip signal providing an indication of particle volume. Detecting the analyte may further comprise counting the aggregates present in the sample.

According to another aspect there is provide a nanoparticle comprising a capture probe for capturing an analyte, wherein the capture probe is configured to act as a centre for controlled aggregation of nanoparticles with the analyte to form an aggregate of particular detectable size and/or shape.

The nanoparticle comprises a rod shaped particle. The nanoparticles may comprise an aspect ratio of greater than 1. The diameter and length of the nanoparticle may be varied as required during manufacture. The nanoparticle may comprise a multi-component rod. The nanoparticle may further comprise a segment defining a location for the capture probe. The nanoparticle may comprise an Ni segment. The location and size of the segment may be controlled as required during manufacture to provide for controlled aggregation of the nanoparticles with an analyte. The location and size of the capture probe may be controlled as required during manufacture to provide for controlled aggregation of the nanoparticles with an analyte. In one arrangement the location and size of the Ni segment may controlled as required during manufacture to provide for controlled aggregation of the nanoparticles with an analyte.

In a first arrangement the capture probe may be provided at one end of the rod shaped particle. The nanoparticles being configured to aggregate end to end with an analyte and similar nanoparticle. In a second arrangement the capture probe may be provided between the rod ends and spaced apart from the rod ends. The nanoparticle being configured to aggregate side by side with an analyte and similar nanoparticle.

The multi-component rod may further comprise a component selected to provide optical and/or magnetic characteristics. The surface of the nanoparticle may comprise a surface modification. The modification may be configured to allow capture of DNA or to allow capture of proteins.

The nanoparticles/s may manufactured by template deposition. The dimensions of the nanoparticles/s may be controlled by template deposition methods for example by control of both the reaction time and the template used. The template may comprise a membrane having regular cylindrical pores, the diameter of the pores controlling the diameter of the growing particle/s. The length of the particles may be determined by the total charge passed during the course of the electro-deposition. The material within the nanoparticles/s may be controlled by varying the solution and potential under which the reaction takes place.

According to a further aspect an assay for determining an analyte may be provided, the assay using nanoparticles according to the present specification comprising a capture probe for capturing said analyte characterized in that said nanoparticles comprise rod shaped particles, said nanoparticles being configured to aggregate to form with said analyte a complex of detectable size and/or shape.

According to a further aspect there is provided a method of detecting an analyte in a sample comprising the steps of: providing nanoparticles having at least one analyte capture probe fixed thereto, the analyte capture probe being capable of binding an analyte;
introducing the nanoparticles into the sample;
allowing the analyte to bind to the at least one analyte capture probe on two nanoparticles to form an analyte bound nanoparticle complex; wherein the nanoparticles are configured to aggregate in a controlled manner with the analyte to form a complex of predetermined shape and/or size;
detecting the analyte bound nanoparticle complex based on the size and/or shape of the complex; and detecting the presence of the analyte.

The nanoparticles may comprise rod shaped nanoparticles.

In one arrangement the presence of the analyte is detected by a nanopore detection system. The size of each complex entering the nonopore detection system as determined by the magnitude of current dip may be measured. The volume a complex obstructs as it traverses the pore being related to the peak height is measured. The full width half maximum (FWHM) being an indication of the time taken for the particle to traverse the pore may be measured. Further the particles passing through the nanopore detection system may be counted sequentially. The method may further comprises determining a concentration of the analyte.

The nanoparticles may comprise first and second rod shaped nanoparticles of first and second lengths, the first and second rod shaped nanoparticles having capture probes configured to capture different analytes and further being configured to aggregate to form different complexes, wherein the complexes are of different shape and/or size.

The nanoparticles may comprise rod shaped nanoparticles and spherical nanoparticles, the rod shaped nanoparticles and spherical nanoparticles comprising capture probes configured to capture different analytes and further being configured to aggregate to form different complexes, wherein the complexes are of different shape and/or size.

BRIEF DESCRIPTION OF THE DRAWINGS

The present invention will now be described with reference to the accompanying drawings in which.

B4 and B5 show that using the magpull strategy the beads may be washed and resuspended before analysis. In B6, the aggregation state of the SPMs was determined using a flow enhanced non-linear magnetophoretic separator (f-NLM) separator and further downstream analyser means.

Figure 1A:
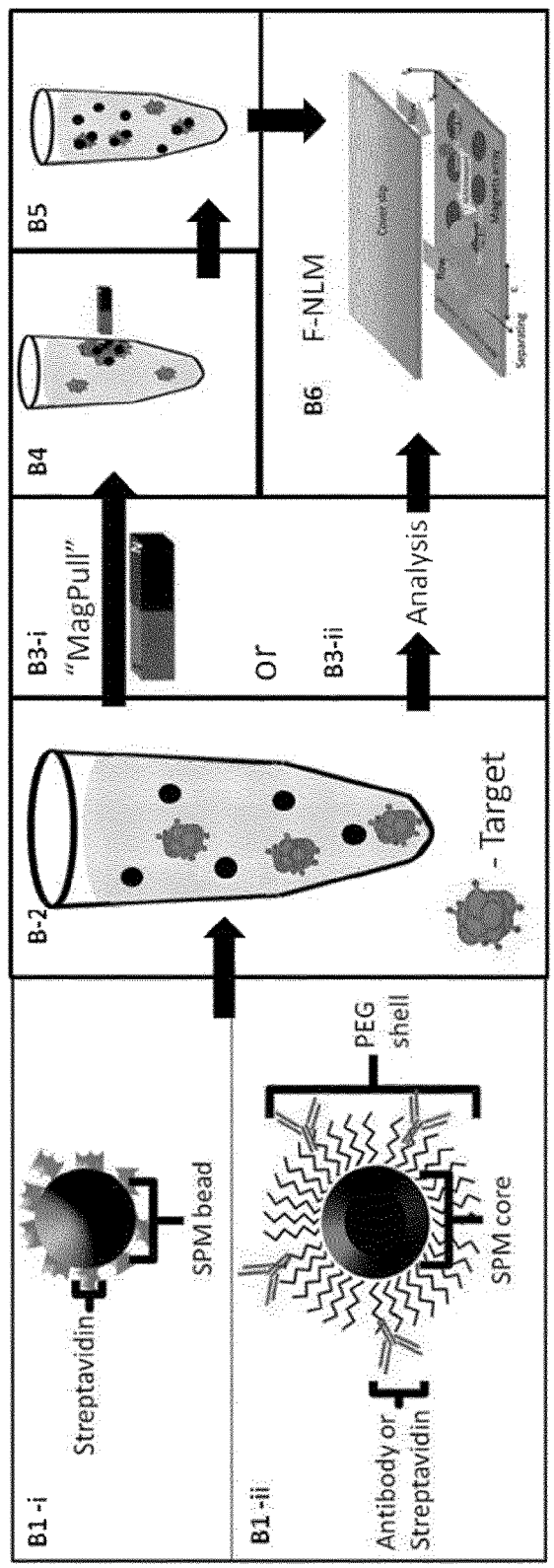
FIG. 1A, which includes multiple panels, shows a schematic of magnetic bead agglutination assay provided upstream of a FNLM system. SPM's were either (B1-i) purchased with a streptavidin monolayer or (B1-ii) carboxyl beads were coated with PEG and conjugated to an antibody of choice. In B-2, SPM's were incubated with target. In B3-i, aggregation of the beads was aided by the use of a magnetic field. B3-ii shows that samples can also be analysed without MBA.
Figure 1B:
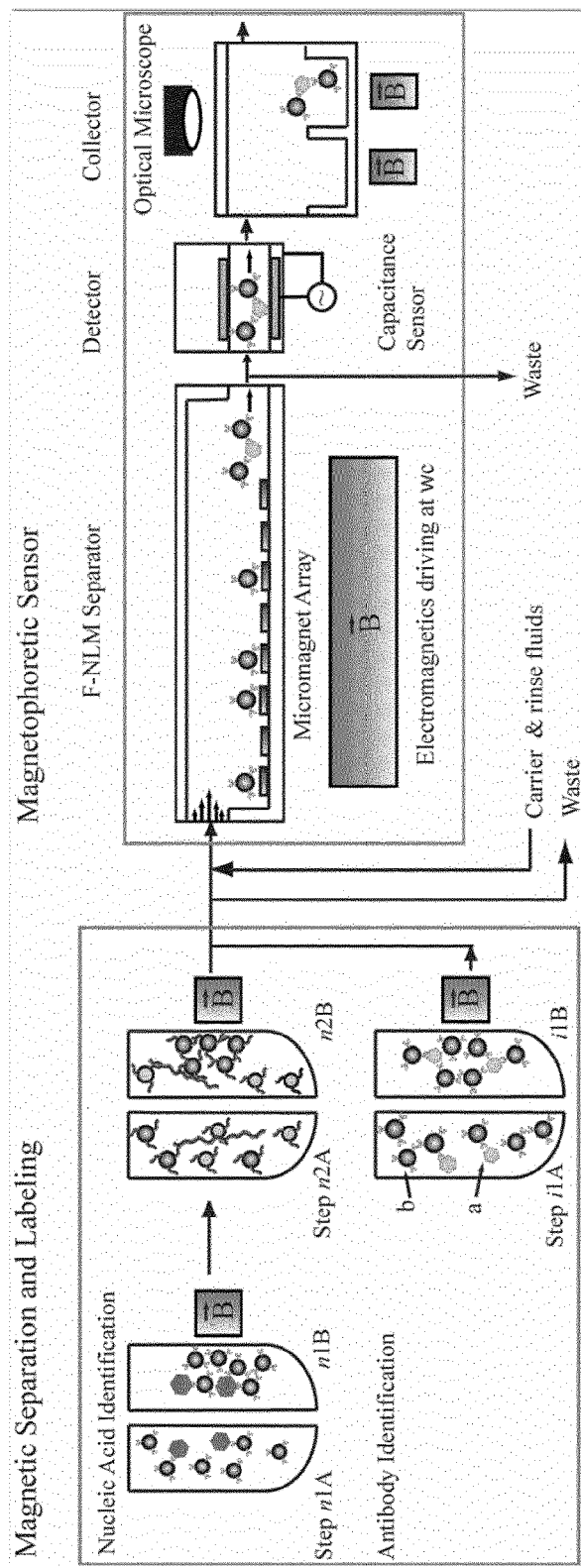

FIG. 1B shows an example of how an F-NLM of B6 of FIG. 1A may be incorporated into a larger analysis arrangement.

Figure 2:
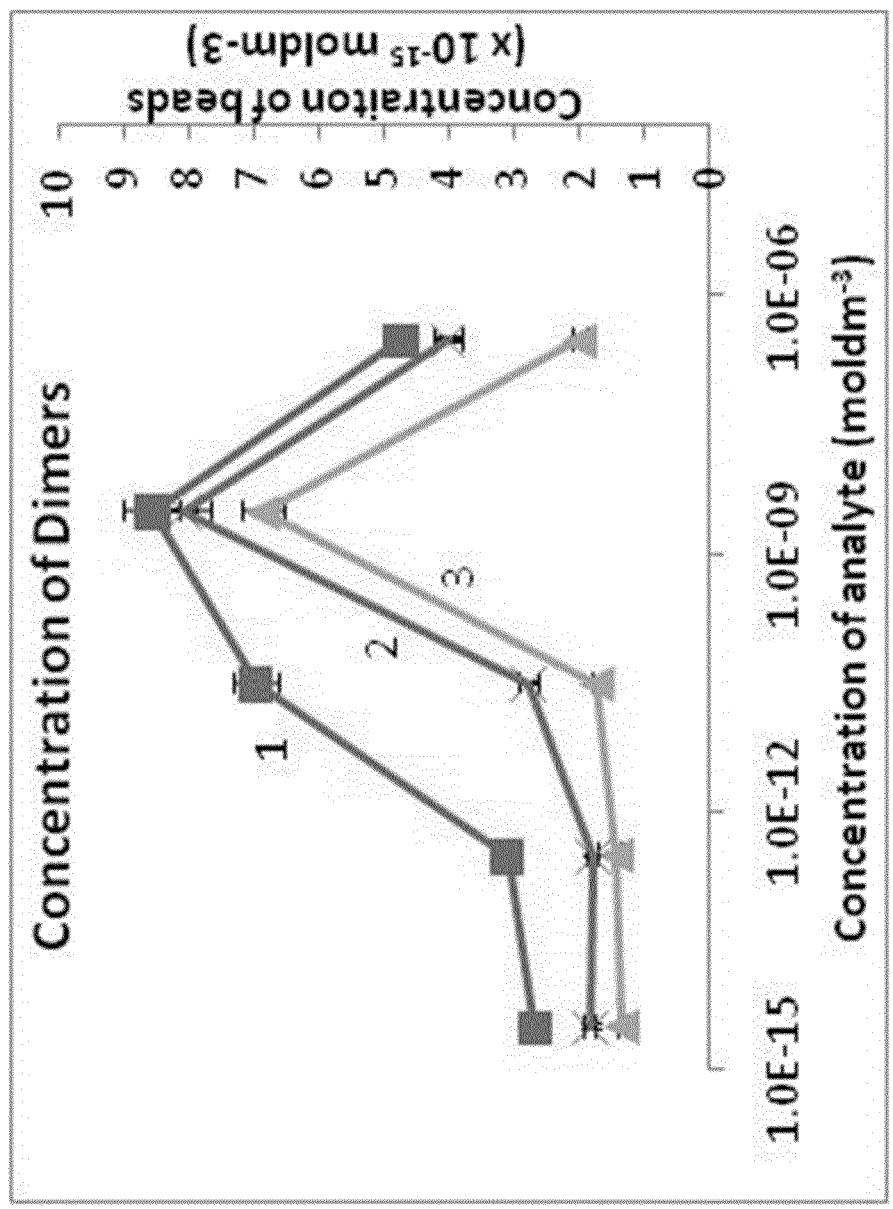

FIG. 2 shows exemplary data indicative of the improvement possible using the aggregation technique of FIG. 1A.

Figure 3A:
Figure 3B:
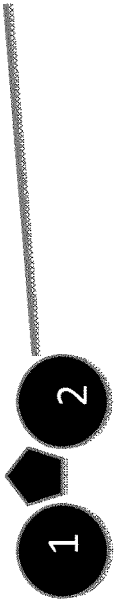
Figure 3C:
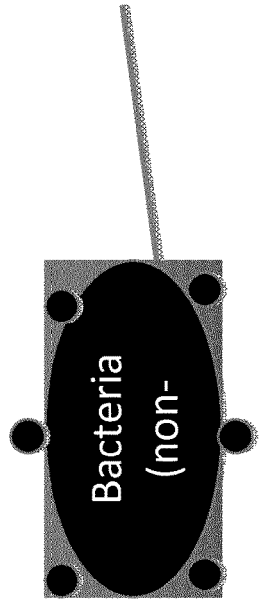
Figure 3D:
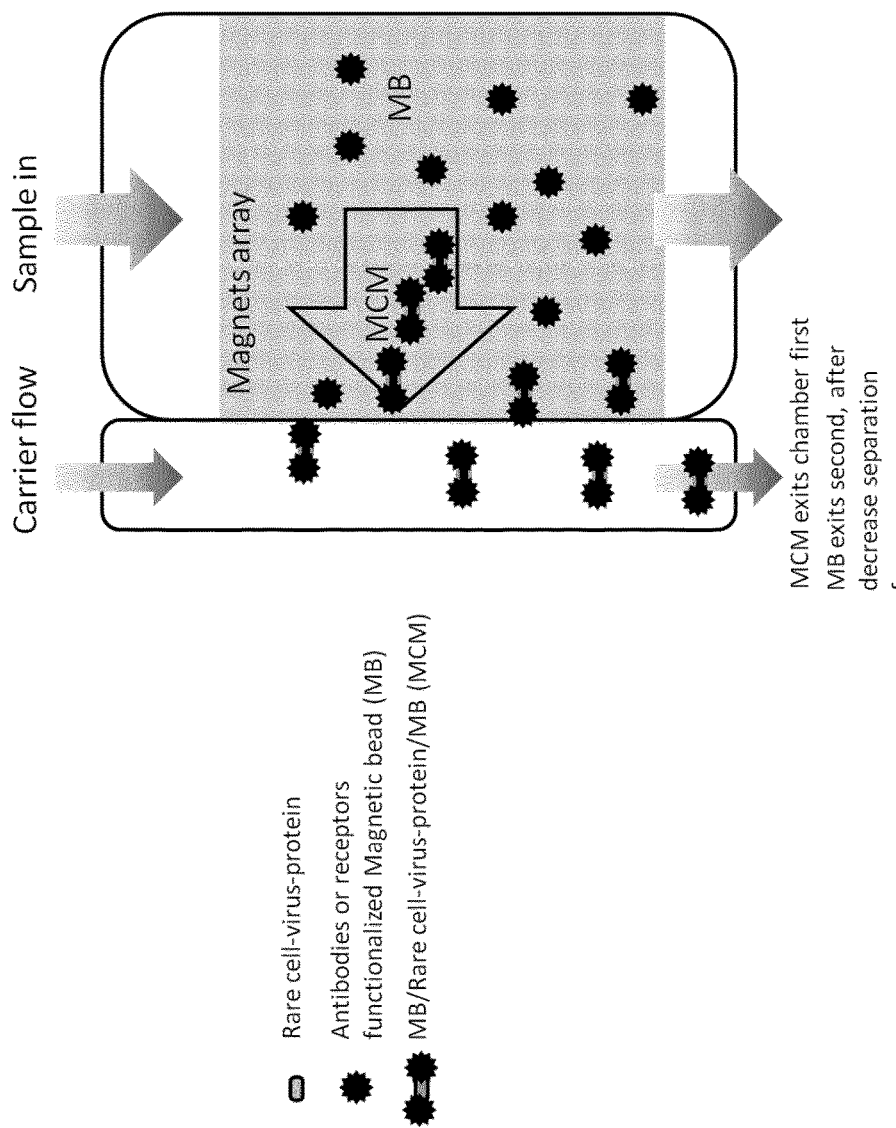
Figure 6:
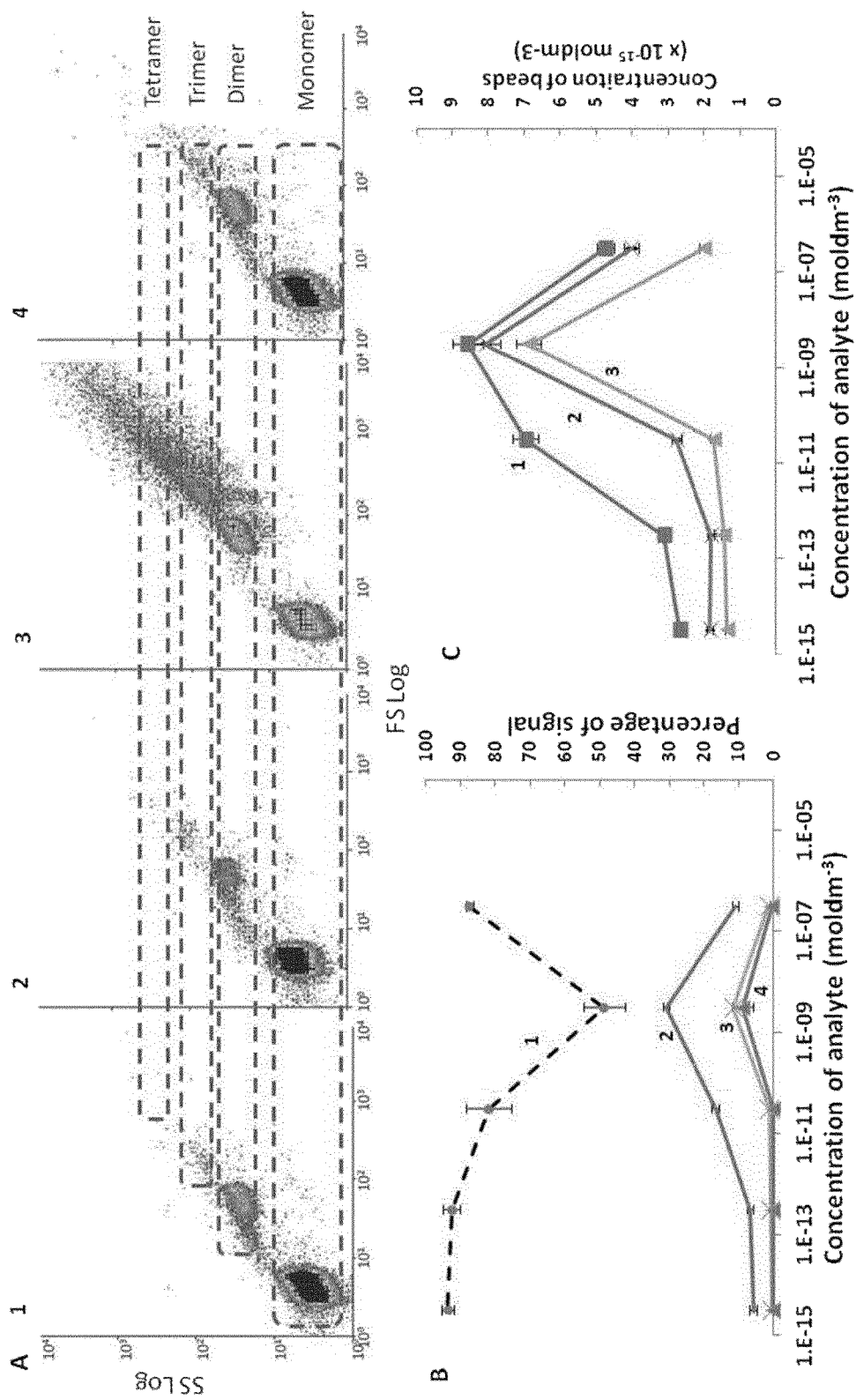

FIGS. 3A, 3B and 3C. FIG. 3A an example illustration of superparamagneic particles functionalized with a receptor which could be an antibody antibody, nucleic acid, protein, peptide, or other molecular receptor; or nonspecific adsorption moiety, i.e, negative or positive moiety, here the pathogen may be virus, protein, etc. FIG. 3B an example illustration is shown of superparamagnetic particles functionalized with more than one receptor which can be an antibody, nucleic acid, protein, peptide, or other molecular receptor; or nonspecific adsorption moiety, i.e, negative or Positive moiety. Referring to FIG. 3C an example illustration is shown superparamagnetic particles functionalized With one (or more) receptors which can be an antibody, nucleic acid, protein, peptide, or other molecular receptor; or nonspecific adsorption moiety, i.e, negative or positive moiety FIG. 3D is an illustrations of example separations using magnetic beads aggregates and an F-NLM separator;

FIGS. 4A-D show schematics of a magnetic bead agglutination—flow cytometry based assay. FIG. 4A illustrates capture of analyte and aggregation of superparamagnetic materials (SPMs) beads using magnetic bead aggregation assay (MBA). FIG. 4B1 SPM's were either (i) purchased with a streptavidin monolayer or (ii) carboxyl beads were coated with PEG and conjugated to an antibody of choice. FIG. 4B2 SPM's were incubated with target. 4B3i Aggregation of the beads was aided by the use of a magnetic field. FIG. 4B3-ii Samples can also be analysed without MBA. FIG. 4B4/B5 Using the magpull strategy the beads may be washed and resuspended before analysis. FIG. 4B6 The aggregation state of the SPMs was determined using flow cytometry; FIG. 4C Schematic of analyte and aggregations of SPMs using MBA including monomers, dimers, trimers and FIG. 4D FC analysis of assays executed using 50 fM of 3 micron streptavidin beads, shown in B1-i, with a binding capacity 75 nM, 30 min reaction time. BBSA at concentrations of 1) $3 \times 10^{-4}$ nM, 2) 0.03 nM, 3) 3 nM, and 4) 300 nM.

Figure 5:
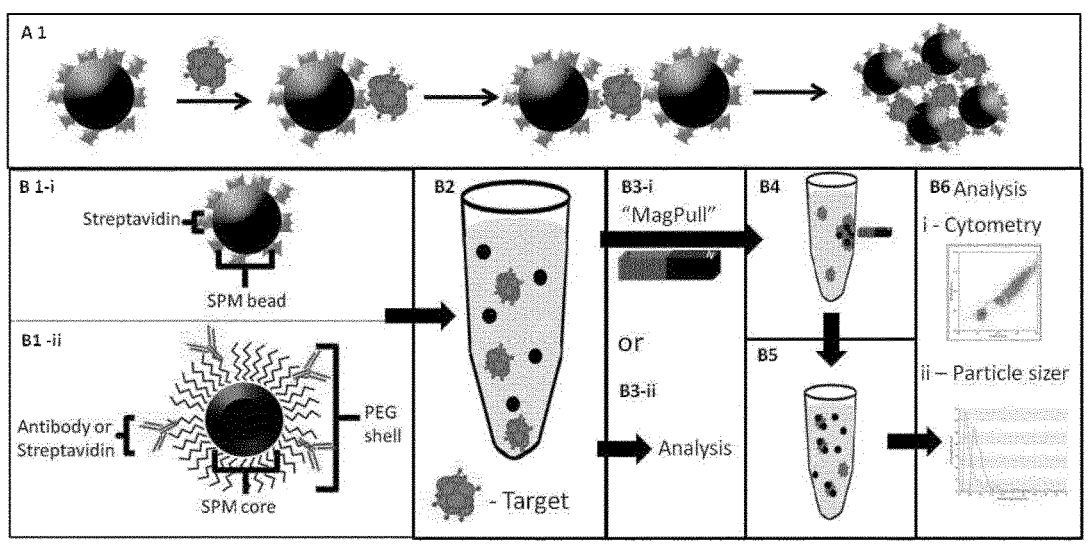

FIG. 5, which includes multiple panels, shows similar schematics of the assay as shown in FIGS. 4A to 4D. FIG. 5, panel A1—Outline of an assay using SPM's, depending on the assay time and bead concentrations the aggregates can be large and contain numerous SPM's. SPM's are either (B1-i) purchased with a streptavidin functionality, or (B1-ii) carboxyl beads from the same supplier are covered with a PEG coating that is later conjugated to the protein of choice. In B2, SPM's are incubated with target. Aggregation of the beads is aided via the use of a "magpull" stage (B3-i), or if required the sample can be analysed immediately (B3-ii). During the "magpull" stage the beads may be washed (B4). Beads are resuspended before analysis (B5). Flow cytometry (B6-i) or particle sizing technology (B6-ii) can be used to count the number of bead aggregates.

FIGS. 6A to 6C are graphs of data results showing the influence of magnetic field and reaction time on the response of the biotin-streptavidin MBA-FC assay (all assays undergo magpull unless specifically stated). FIG. 6A FC analysis of assays executed using 50 fM of 3 μm streptavidin beads with a binding capacity 75 nM, 30 min reaction time. BBSA at concentrations of 1) 3×10-4 nM, 2) 0.03 nM, 3) 3 nM, and 4) 300 nM. FIG. 6B Distribution of monomers (1), dimers (2), trimers (3), and tetramers (4) for the reaction conditions described above. FIG. 6C Concentration of dimers in MBA as a function of analyte concentration for a 30 min reaction with MBA (1), 5 min reaction with MBA (2), and 5 min reaction without magnetic field (3). Blank assays were found to have aggregation levels below 3±2% in all assays in this study.

FIGS. 7A and B are graphs of data results showing the influence of bead properties on the response of the biotin-streptavidin MBA-FC assay. FIG. 7A Distribution of 3 μm bead monomers (denoted with *) and dimers as the bead concentration and binding capacity are varied. Curves 1 and 1*—50 fM bead concentration, 75 nM binding capacity. Curves 2 and 2*—50 fM bead concentration, binding capacity of 8 nM. Curves 3 and 3*—5 fM bead concentration, binding capacity of 7 nM. FIG. 7B Formation of 1 μm bead monomers (denoted *) and tetramers as the bead concentration and binding capacity of the beads are varied. Curve 1 and 1*—5 fM bead concentration, binding capacity 0.52 nM. Curves 2 and 2*—50 fM bead concentration, binding capacity 5.2 nM. Curves 3 and 3*—500 fM bead concentration, binding capacity 52 nM These reactions were carried out in PBST buffer for 30 mins followed by magpull and FC analysis. Blank assays were found to have aggregation levels below 3±2% in all assays in this study.

FIGS. 8A and B are graphs showing HSV-1 and 2 MBA-FC assay—Curve 1—monomers, 2—dimers, 3—trimers and 4—tetramers of SPMs. FIG. 8A Formation of aggregates of 3 μm SPMs as a function of HSV-2 antigen concentration in PBST, 50 fM bead concentration, binding capacity of 3 nM. 6B Formation of aggregates of 1 μm SPMs as a function of HSV-1 antigen concentration in PBST, 500 fM bead concentration, binding capacity of 3 nM. In each assay the SPMs were reacted with the analytes for 30 mins in PBST. Blank assays were found to have a aggregation level below 3±2%.

Figure 9:
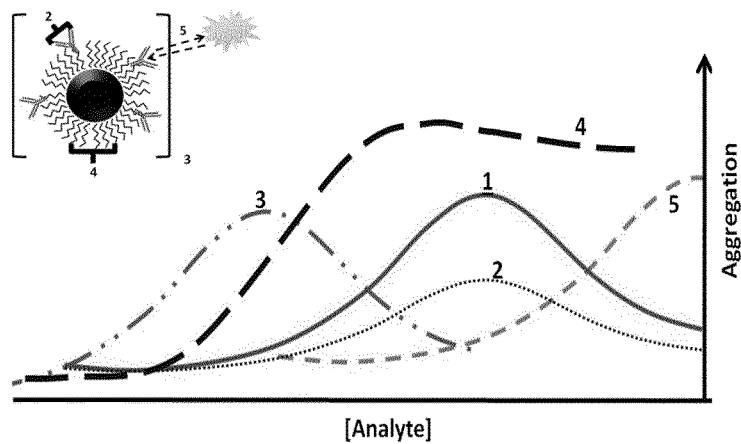

FIG. 9 MBA aggregation key parameters resulting from change in the physical and chemical properties of the SPMs. 1—Reference bead diameter (w), bead number (x), binding capacity (y), avidity (z). 2—Decrease y, constant w, x and z. 3—Decrease x, constant w, y and z. 4—Decrease w, constant x, y and z. 5—Constant w, x and y decrease z.

Figure 10:
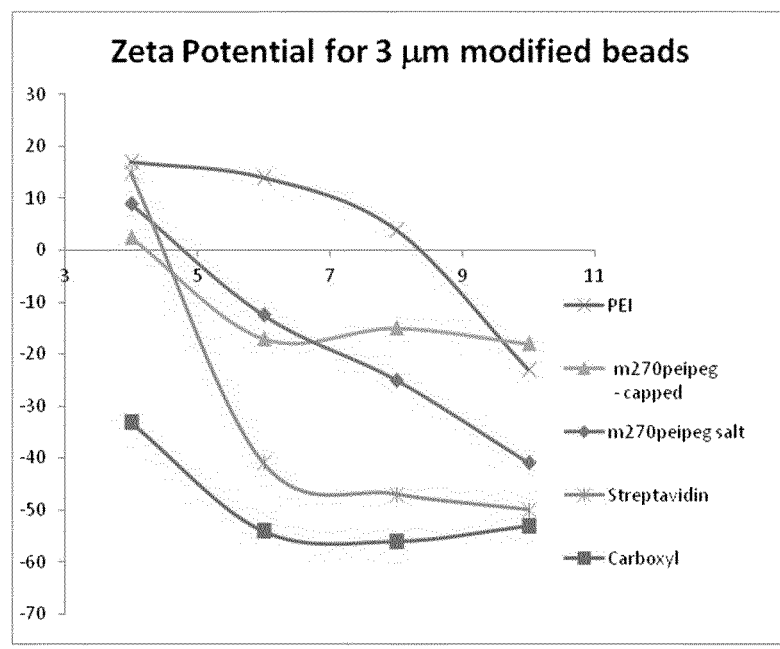

FIG. 10 is a graph showing Zeta potential for beads used in the assays.

Figure 11:
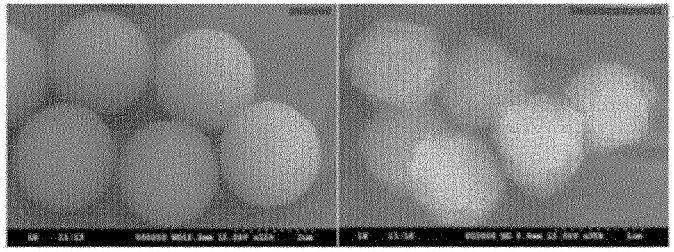

FIG. 11 shows two SEM images of SPB's. (left) Invitrogen m270, (right) Invitrogen Myone (Scale bar is equal to one micron).

Figure 12:
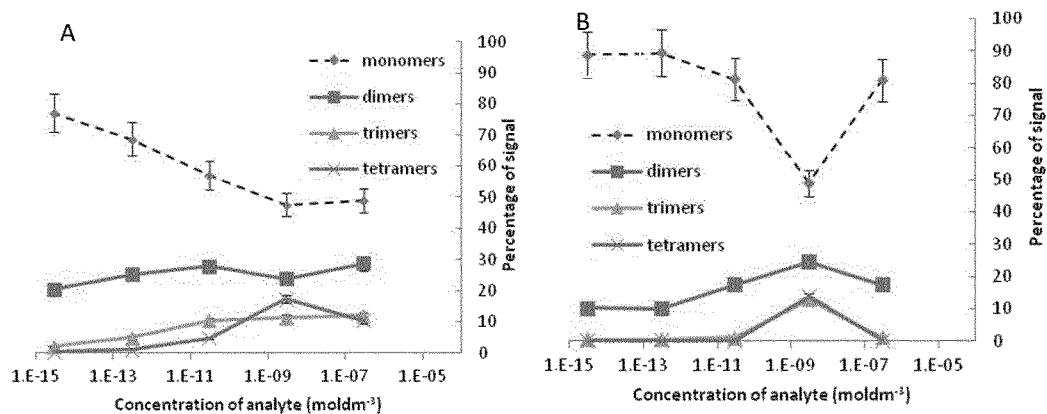

FIGS. 12 A and B are graphs showing Flow cytometry data for 1 mm streptavidin beads—30 min assay, Percentage of aggregates of beads as a function of analyte concentration. Bead concentration of 500 fM bead concentration. 30 min assay A—with magpull, B—no magpull.

FIG. 13 PEG modified 3 micron beads, 50 fM—number of monomers (A) and dimers (B) in sample after assay time 30 mins, (with magpull). Curves 1, 2 and 3, PEG modified beads coated with Streptavidin binding capacity 1=1 nM, 2=7 nM, 3=12 nM, assay ran in PBST. Curves 4 and 5 were ran in BSA spiked FSA samples for 30 mins, 4 PEG modified bead with a binding capacity of 7 nM, 5 commercial unmodified streptavidin bead, binding capacity 70 nM.

Figure 14:
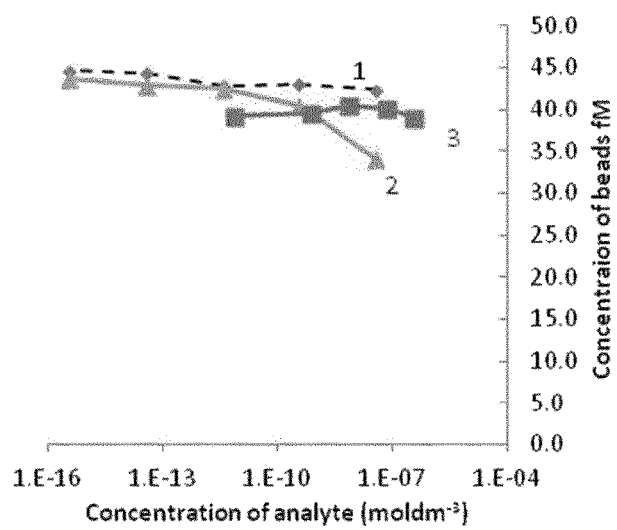

FIG. 14 Relative fraction of monomers for HSV-2 assay using 3 micron PEG modified beads, assay time 30 mins. 1—Polyclonal antibodies, with magpull. 2—Monoclonal antibody modified beads, with magpull. 3—Monoclonal antibody modified beads without magpull.

Figure 15:
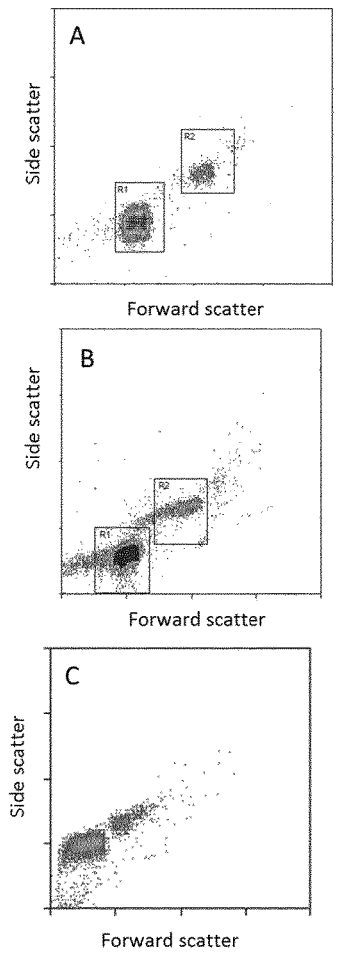

FIG. 15 Cytometry scatter plots for "Blank" samples. A) 3 micron Streptavidin beads direct from supplier, R2 contains the data from nonspecific aggregation, 8% of the population. B) 3 micron PEG modified Streptavidin beads, R2 contains the data from nonspecific aggregation, 3% of the population. C) 1 micron commercial Streptavidin beads.

FIGS. 16 A to C show examples of tagged particles that may be usefully employed within the context of the present teaching.

Figure 17:
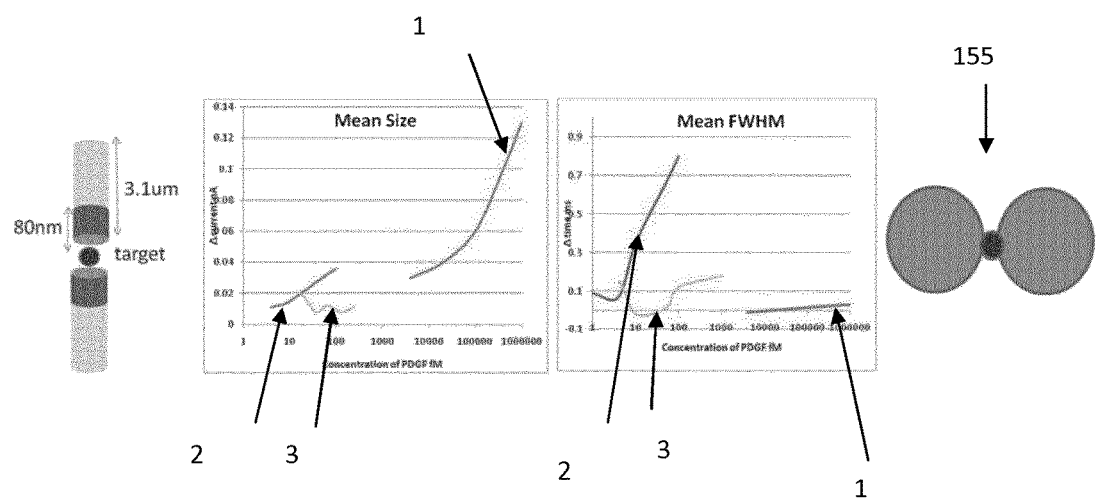

FIG. 17 the graph on the left shows the change in current as aggregates particles moved through a pore—red and yellow (curves 2 and 3) for rods and green (curve 1) for beads. As shown, the size of the aggregates clearly increased as the concentration of analyte was added increased for the rods and beads. The sensitivity of the assay for the beads is such that is possible to measure the presence of PDGF at 10 pM concentration for the beads. The FWHM signal (graph on the right) compares signals for aggregates of beads and rods. It is noted that the FWHM signal for the rods is greater for the rods than beads as the rods not form long chains.

Figure 18:
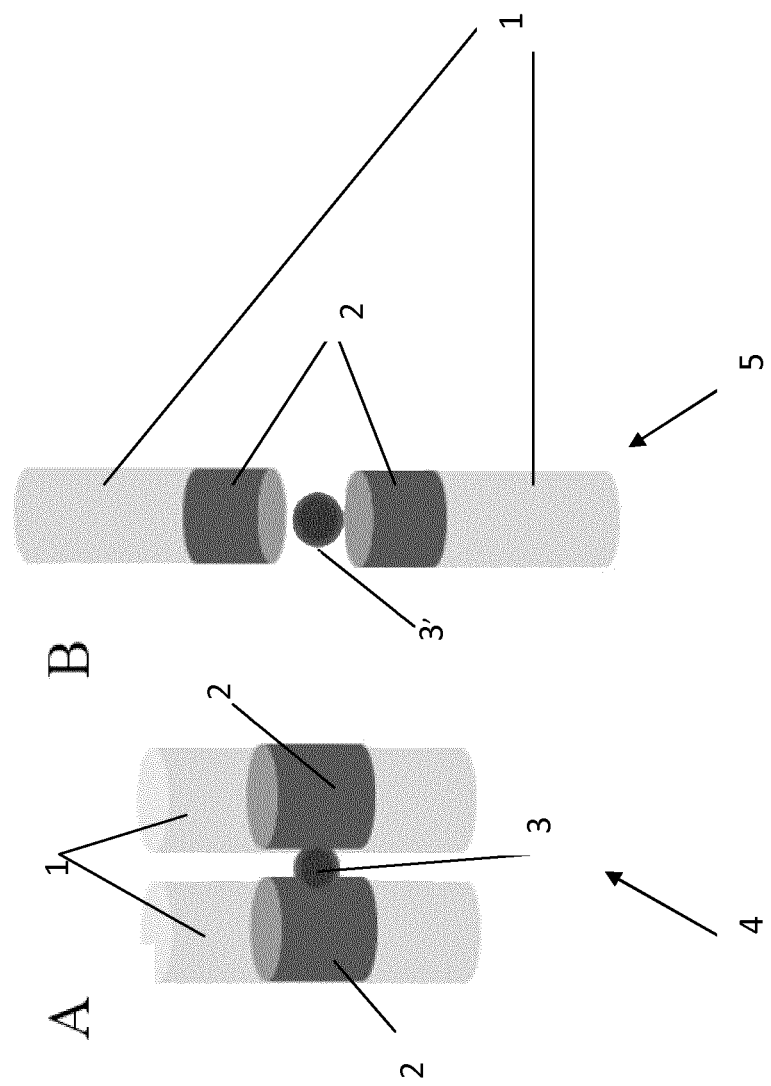
Figures 19A, 19B, 19C:
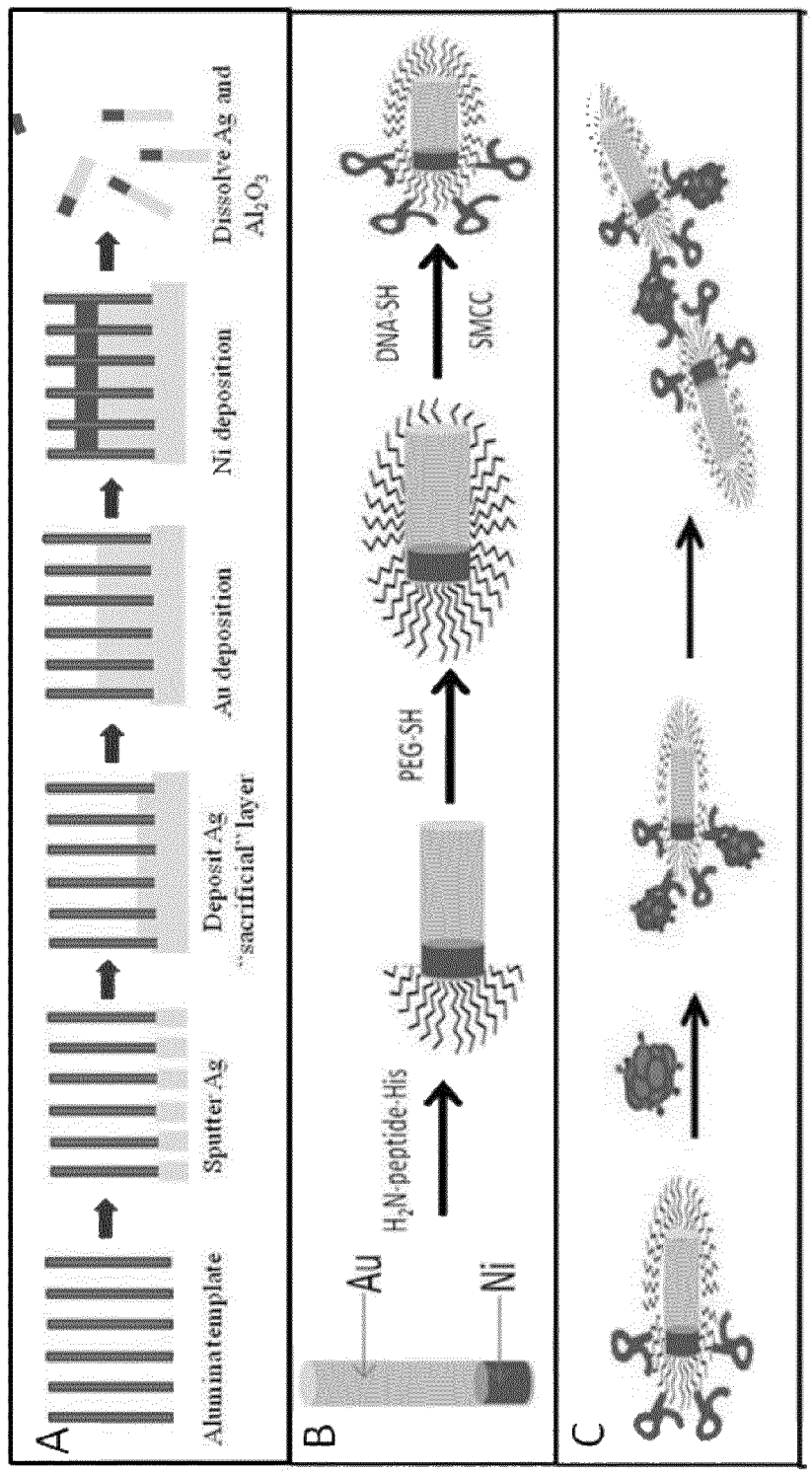

FIG. 18 Schematic of two assay techniques a—aggregation leading to an increase in size, b—End-on-End aggregation;

FIGS. 19A, 19B and 19C shows schematically the particle synthesis. FIG. 19A—Example template deposition method for producing rod shaped particles of an embodiment according to the present specification including the steps of (i) providing an alumina template, (ii) sputtering with Ag, (iii) depositing Ag "sacrificial layer, (iv) Au Deposition, (v) Ni deposition and (vi) dissolving Ag and $Al_2O_3$. FIG. 19B—Overview of the surface chemistry stages (i) providing Au rod with Ni segment, Ni segments are modified with a His-tagged peptide, the Au segments are modified with PEG-SH molecules, DNA-SH SMCC. FIG. 19C—Example schematic of the assay, showing end on end aggregation of two nanoparticles (rods) with analyte.

FIGS. 20A and 20B Overview of the nanopore detection process. FIG. 20A—image of a suitable example detection system in this case a nanopore detection instrument. In the middle of the spetum an individual pore enables particles to pass through the membrane. Side on image on the membrane and pore, the sample is placed into the upper fluid cell, and the particles move down through the pore under the influence of gravity into the lower fluid cell. FIG. 20B—shows an example of baseline current and "blockade" events (dips in current) that are caused by particles. Each dip contains information on particle size and FWHM;

FIGS. 21A, 21B, 21C and 21D. Purple (i)=sphere (2 μm diameter), Green (ii)=sphere (0.955 □μm diameter), blue (iii)=Au rod (4.7 μm length-CV 14%, 290 nm diameter-CV 15%), Red=(iv) Au rod (2.15 μm length-CV 20%, 325 nm diameter-CV 14%). FIG. 22A, Mode $\Delta i_p$ values as pore size is varied, fixed potential of 0.12V, FIG. 22B, Mode FWHM values as pore size is varied, fixed potential of 0.12V. FIG. 22C, Δip histogram for the samples run at a stretch of 44.5 mm in part A. FIG. 22D FWHM histogram for samples run at a stretch of 44.5 mm part B.

Figure 23:
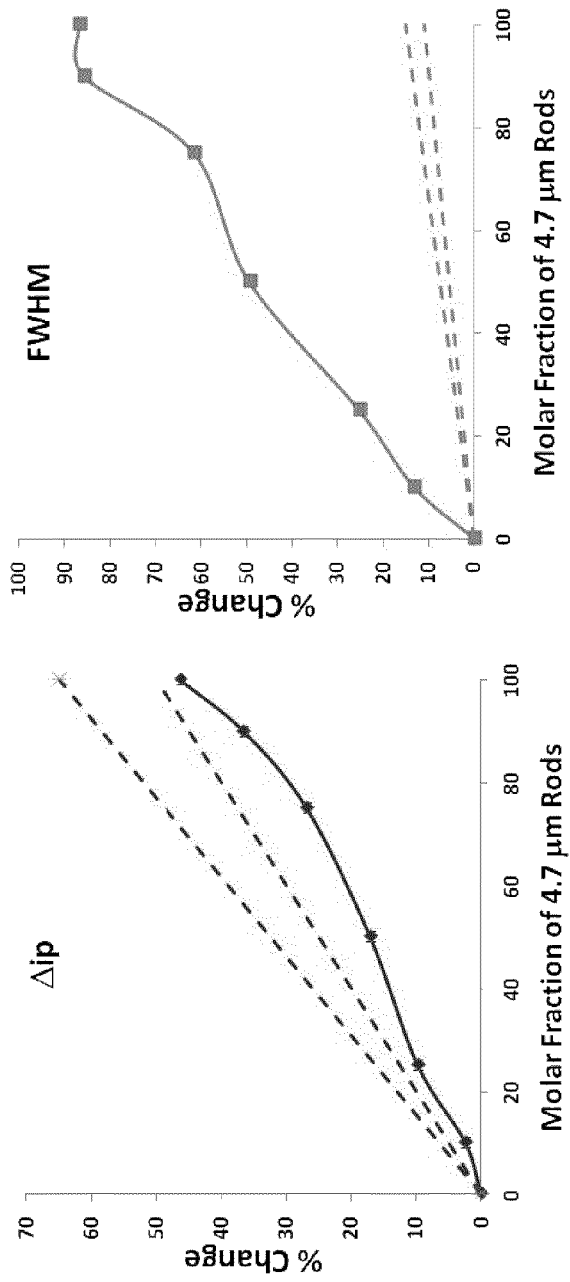

FIG. 22A Height (nA) versus % population. Insert—average size (y axis) over the course of the experiment in seconds (x axis). FIG. 22B FWHM (ms) vents % population;

FIG. 23 Changes in Δip, and FWHM, as mole fraction of 4.7 μm rods is increased from a solution containing initially only the 2.15 μm rods. Dashed regions indicate the maximum and minimum values predicted from the model given the CV of the particle set. Error bars show the d25 and d75 values for the measured population;

FIGS. 24a, 24b, 24c, 24d are an overview of the surface chemistry modifications and assays. FIG. 24a—The surfaces of the Ni segments are modified with a His-tagged peptide, the Au segments are modified with PEG-SH molecules. FIG. 24b—Confirmation of localised surface chemistries with fluorescent modified Ni segments. FIG. 24c—Schematic of the aggregation assay via "end-on-end" aggregation. FIG. 24d—Schematic of the aggregation assay via "Side-on" aggregation.

Figures 25A, 25B, 25C, 25D:
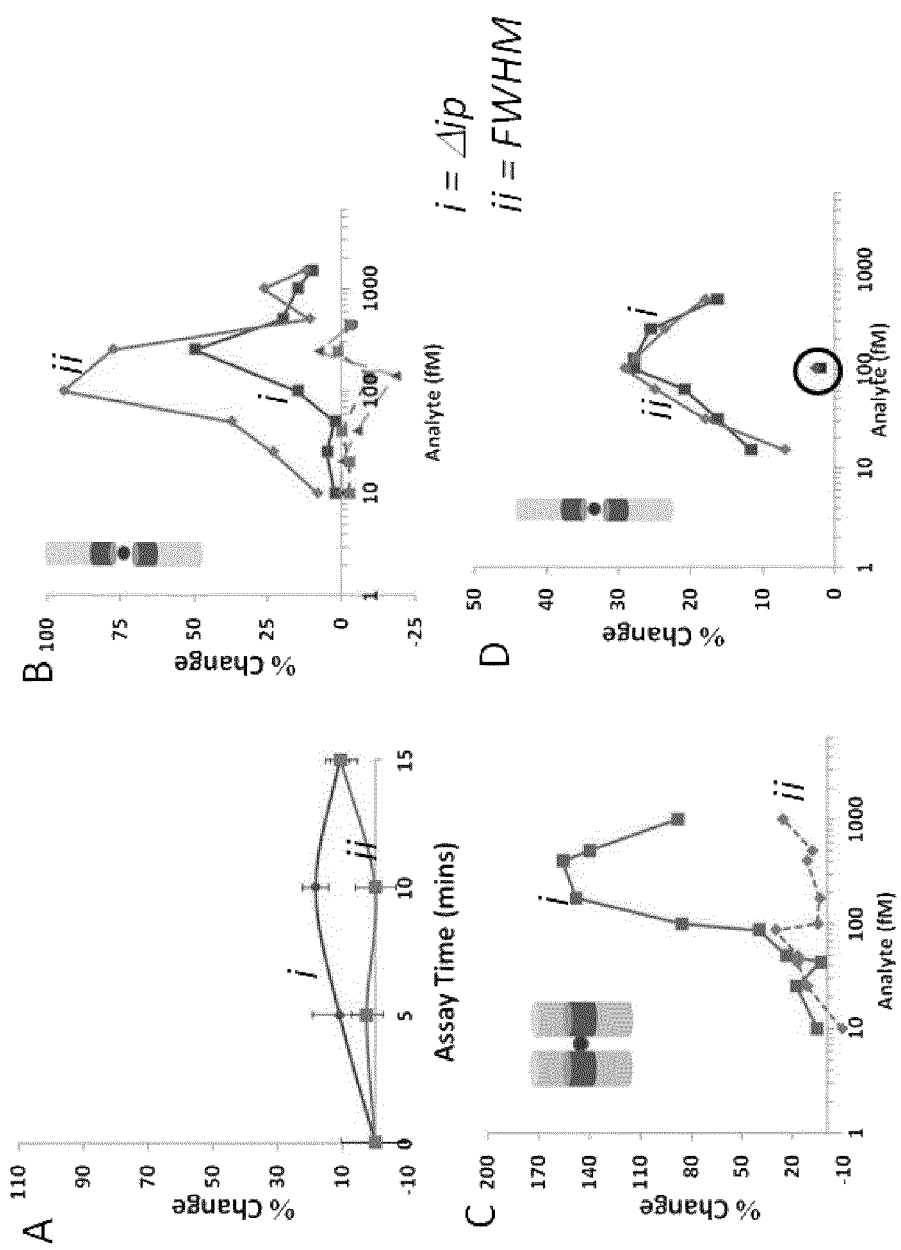

FIGS. 25A, 25B, 25C and 25D. Performed using a NP1000, stretch=44.5 mm=Potential=0.14, red lines indicate $\Delta i_p$, blue lines indicate FWHM. FIG. 25A, AuNi rods, 1.23 μm in length (CV 20%, Ni content 15% by length), 400 fM, % Change $\Delta i_p$ and FWHM as assay time is increased in the absence of an analyte. FIG. 25B, Same rods as A, assay time 10 mins. Ni segments functionalised with Avidin. Dashed lines represent a 10 min assay with a non biotinylated target. FIG. 25C, AuNiAu rods, 0.82 μm in length (CV 14%, Ni content 18% by length), 500 fM, assay time 10 mins. FIG. 25D, AuNi rods, 1.1 μm in length (CV 20%, Ni content 14% by length), 150 fM assay time 10 mins. Ni segments functionalised with PDGF aptamer. The circled data points plotted at 100 fM indicate the change in FWHM and Δip for the same rods using a control protein

DETAILED DESCRIPTION OF THE DRAWINGS

System

Referring to the drawings 1 to 17, and initially in particular to FIGS. 1A, 1B, 2 and 3A and 3B a separation and analysis system 100 comprising a magnetic bead agglutination assay (MBA) 110 is described.

Referring to the attached drawings and initially in particular FIGS. 1A, 1B, 3A and 3B, FIGS. 4A to 4D and 5 there is provided a separation and analysis system 100. The system is used for performing separation and analysis of an analyte 135 in a sample 130. It will be appreciated that the specifics of this separation system and detection 100 are provided to assist in an understanding of the present teaching and in no way should be construed as limiting the teaching to this example.

The magnetic bead agglutination assay 110 comprises a reaction chamber 120. Magnetic beads 140 are provide for reaction with a sample 130 including an analyte 135 in the reaction chamber to form a bead suspension 150. The magnetic beads preferably comprise superparamagnetic beads most preferably superparamagnetic micro-beads (SPMs) 140. The magnetic or superparamagnetic beads 140 are functionalised beads comprising a capture probe or reactor 145 capable of binding with an analyte 135. The beads 140 may comprise one or more antibodies or receptors of choice to magnetic or nonmagnetic beads. The beads may comprise a specific capture probe 145 for binding with a target analyte 135. The beads 140 may comprise (i) a streptavidin monolayer or (ii) carboxyl beads coated with PEG and conjugated to an antibody of choice. The beads may comprise a negative carboxyl surface, modified to contain amine groups which are reacted with a PEG polymer as a protective layer, as discussed further later. In which case any unreacted amine groups are converted to hydroxyl groups. This approach is to reduce the number of non-specific aggregates. While in the example noted above the beads may be coated with a protective PEG layer, it will be appreciated that other suitable protective layers may also be used. The magnetic beads 140 are typically of diameter in the range of 10 nm to 10,000 nm, preferably in the range of 0.1 to 5 microns, most preferably 0.2 to 2 microns diameter.

Referring to FIGS. 3A to 3C, it is noted that the methods and system of the present specification refer to magnetic beads and magnetic bead aggregations, examples of which are initially described with reference to FIG. 3. In the present specification the particles of a sample are variously referred to as superparamagnetic particles or superparamagnetic beads, superparamagnetic micro-particles or superparamagnetic microbeads (SPMs), magnetic beads, magnetic particles, particles, beads, micro-beads, micro-particles, and analytes. The superparamagnetic beads/particles typically range in size in the order of 1 nm to 100 nm diameter, preferably 1-10 microns, most preferably 1-3 microns. The magnetic beads are reacted with a target analyte in a sample to form aggregates alternatively referred to herein as aggregations or agglutinations, aggregates or agglutinates. In the present specification, the magnetic particles or beads are functionalised to enable binding or capture with an analyte. The analyte may be a specific target analyte or an unspecified analyte. The beads are functionalised beads comprising a capture probe or reactor for binding with an analyte. The terms capture probe and receptor have been used in the specification. Example aggregates may include a dimer or sandwich assay in which the analyte is bound between two of the magnetic particles. Another example may include a monomer in which a magnetic particle is bound to an analyte. Further examples may include trimers and tetramers in which the analyte is bound to three or four magnetic particles. Further, the aggregations (or agglutinations) 155 can be large and contain numerous super-paramagnetic beads (SPM's). See example aggregate FIG. 3C. It will be appreciated that various other alternative types of aggregates 155 may also be formed. The various type aggregates 155 are detectable on the basis of physical properties thereof. The physical properties may include volume or magnetic moment or size. It will be appreciated that a magnetic particle may also be bound to a non-magnetic particle and analyte. An example may be a bacteria or cell (e.g. a stem cell), bound to a magnetic particle or bead and a fluorescent particle. It is also possible to use magnetic particles of different colours to allow identification and resolution of analytes on the basis of colour. The method and system provided in accordance with the present teaching which provides for identification of particles on the basis of the physical properties of the aggregates noted above on an aggregate by aggregate basis. Further it will be appreciated that identification on the basis of different colour or size for example by use of the heretofore described monitoring or sensor means.

Referring to FIG. 3A an example illustration of superparamagneic particles functionalized with a receptor which could be an antibody antibody, nucleic acid, protein, peptide, or other molecular receptor; or nonspecific adsorption moiety, i.e, negative or positive moiety. Here the pathogen may be virus, protein, etc. Referring to FIG. 3B an example illustration is shown of superparamagnetic particles functionalized with more than one receptor which can be an antibody, nucleic acid, protein, peptide, or other molecular receptor; or nonspecific adsorption moiety, i.e, negative or Positive moiety. Referring to FIG. 3C an example illustration is shown superparamagnetic particles functionalized with one (or more) receptors which can be an antibody, nucleic acid, protein, peptide, or other molecular receptor; or nonspecific adsorption moiety, i.e, negative or positive moiety.

The magnetic bead agglutination assay 110 further comprises an aggregator or aggregation means 160 for aggregating particles prior to analysis to drive the clustering and aggregation of magnetic particles 140 around the analyte cells 135. The aggregation means 160 comprises a magnetic means 165 for applying an external magnetic force or magnetic field to the particles 140 in the reaction chamber 120 subsequent to the step of reacting the particles with the sample. The magnetic force may comprise a magnetic gradient. The magnetic force may comprise a time varying magnetic field. The magnetic force is applied to the particle suspension 150 in the reaction chamber to separate the beads and accelerate the rate of bead-bead interaction. This controlled application of a magnetic force to the particle suspension 150 provides for controlled aggregation of the superparamagnetic particles 145 therein. The aggregation of the superparamagnetic particles provides formation of magnetic bead agglutinates or magnetic bead aggregates 155. The application of an external magnetic field to the suspension has been according to the method of the present specification has been described herein as the magpull step (described in further detail below) which provides an enhancement of the aggregation. When the magpull step is applied, the number of measured aggregates is greater for lower analyte concentrations. The magpull step further provides an increase in the rate of aggregation of the particles.

The system 100 further comprises an analyser or detection means 200 provided downstream of the magnetic bead agglutination assay 110. The analyser or detection means 200 is configured to perform analysis of the magnetic bead aggregates. The analysis is based on the characterization of the agglutination 155. The analysis step comprises measuring the bead aggregation or aggregates on an aggregate-by-aggregate basis. The characterization of the bead aggregation is based on using the physical properties of the bead aggregates, i.e., measuring magnetic moment (FNLM) or measuring volume (Flow cytometry (FC), FNLM) or aggregate size or shape.

It will be appreciated that for a calibrated magnetic bead assay, physical properties for aggregates of magnetic beads with target analytes will be predefined. Physical properties being for example the magnetic moment or volume of monomers, dimmers, trimers, tetramers etc providing for characterisation of the agglutination on an aggregate by aggregate or particle by particle basis.

The aggregates 155 of particles 140 that have formed through the reaction with the analyte 135 are detected on an aggregate 155 by aggregate 155 basis for example using an optical detector. The optical detector may comprise a flow cytometer:

the external magnetic field 165 for mag pull is released and the particles/aggregates 155 are isolated by moving them into 'chambers' in which they can be sensed.

For example, in the optical detection or flow cytometry system 250 this is achieved by injecting the sample into a flow stream that focuses the particles/aggregates 155. This is a preferred approach as it makes it possible to identify in the range of 1,000 to 100,000 particle aggregates/min, preferably 10,000 to 100,000.

In another approach, the particles/aggregates 155 are forced through a pore or a number of parallel pores.

A pore detector is described in further detail below with reference to FIGS. 18 to 26. It will be appreciated that details of the detection based on the pore detector described are similarly applicable for detection of aggregates as described here.

A further approach would be to do the detection on an NLM chip. In that case, application of a local magnetic will allow the particle aggregates to be sensed on individual micromagnets in the chip. For example, of the order of 10,000 to 1,000,000 individual particle aggregates could be sensed on a large micro-magnet array, preferably 10,000 to 100,000.

Further, as noted above the assay 110 may comprise a magnetic particle 140 (SPM) of a first type having a capture probe 145 for binding with a first analyte 135. It will be appreciated that the assay may comprise a magnetic particle 140' of a second type having a capture probe 145' for binding a different analyte 135'.

Also it will be appreciated that a magnetic particle 140 may be bound to a non-magnetic particle and analyte. Such an example could be a bacteria or cell (e.g. a stem cell), bound to a magnetic particles or beads and a fluorescent particle. It is also possible to use magnetic particles of different colours to allow identification and resolution of analytes on the basis of colour.

As the system and method described provide for characterisation of an agglutination on an aggregate by aggregate basis and/or a particle by particle basis it will be appreciated that the system and method is scalable for multiplexed characterisation of an agglutination.

Referring to FIG. 4 the analyzer or detection means 200 comprises a flow cytometer 250.

Referring to FIGS. 1A and 1B, alternative detection means are provided, the detection means may comprise a flow enhanced non-linear magnetophoretic detector (F-NLM detector). F-NLM separators and detection arrangements are described in detail in co-pending WO2012004363 herein incorporated by reference.

In a further alternative arrangement as described with reference to FIG. 5 a particle sizer 270 e.g. a coulter detection means or a pore detection means may be provided.

The method may further comprise the step of transporting the magnetic bead aggregates from the reaction chamber to the detection means for detection if required.

In which case the detecting the aggregates on an aggregate by aggregate basis involves releasing the external magnetic field which was applied for the aggregating step and isolating the aggregates by transporting the aggregates to the detector for sensing. The detection may be an optical detection system and isolating the aggregates for detection may be by transporting them to chambers for sensing. The transporting may be by injecting the sample into a flow stream. The flow stream effectively focuses the aggregates. Alternatively the transporting is by flow from the reaction chamber. The transporting may be by hydrodynamic flow. The transporting may be by gravity.

As noted previously the detection means may comprises an optical detection means for example detection using a flow cytometer has been described. Such optical detection means is configured to identify in the range of 1000 to 100,000 particle aggregates/min, preferably 10,000 to 100,000 particle aggregates/min.

The detection means comprises a particle sizer or pore detection means see FIG. 5. In which case the transporting may be forcing the aggregates 155 through a pore or a number of parallel pores for multiplex detection. Pore detection is described in further detail with respect to FIGS. 18 to 25. However, it will be understood that pore detection means may also be applied to detecting aggregates in the present method. FIG. 17 shows graphically data based on detection of a magnetic bead aggregate 155.

The detection means may comprise an NLM chip with the aggregates being detected on the chip. The application of the local magnetic field allows the particle aggregates to be sensed on individual micromagnets. The aggregates are detected on the chip using an optical detector or magnetometer. The NLM detection means is configured to identify of the order of 1000-1,000,000 individual particle aggregates on a large micro-magnet array, preferably 10,000 to 100,000, depending on the form of the micro-magnet array.

Further the analysing means or detection means may comprise an F-NLM separator (see WO2012004363) for separating the aggregates See FIG. 1B with a detection means for example an optical detection means for detecting the aggregates on an aggregate basis.

Referring to FIGS. 6 to 9 below the results analysis of different exemplary magnetic bead agglutination assay systems 100 according to the present specification and using the flow cytometer or F-NLM detections means 200 are described in further detail to assist in the understanding of the system and method and to demonstrate practically the sensitivity and exemplary run times.

Further, it is noted that in an arrangement according to the present specification, as shown in FIG. 1B the separation and detection system 100 may comprise a chip assembly device 500 for use in separating first and second particle 145, 145' types provided within a sample 130. The chip assembly device comprises a magnetic bead agglutination assay 110 and an F-NLM separator 260 (as described in detail in co-pending WO2012004363) based assay system 100 and detection means for example optical detection means.

It will be appreciated that alternative chip assembly devices 500 according to the present specification may also be provided.

The present specification further provides a device or kit for the determination, by magnetic particle agglutination, the presence of an analyte in a sample, characterized in that it includes:

a) a reaction chamber for reacting a sample containing a target analyte with the magnetic particles in the presence of a magnetic field to form magnetic particle agglutinates, the magnetic particles comprising a capture probe for capturing a target analyte to form an agglutinate, b) a detector configured to characterize the magnetic particle agglutinate based on measuring physical properties of said magnetic particle agglutinate. The detectable physical properties may be magnetic moment and/or volume.

Referring to FIGS. 4A to 4D an arrangement of a magnetic bead agglutination—flow cytometry based assay system 100 is described. As shown in FIG. 4A in reaction chamber 120 sample 130 including analyte 135 is provided to magnetic bead agglutination assay 110. The agglutination assay 110 comprises magnetic beads 140. The magnetic beads 140 are preferably superparamagnetic particles 140 comprising capture probe 145 are reacted with the sample to form magnetic bead suspension 150. Analyte 135 is captured and super paramagnetic particles 140 are aggregated to form an aggregation or agglutination 155 of superparamagnetic particle (SPMs) aggregates using the magnetic bead agglutination assay. The aggregation step is preferably performed in the presence of an external magnetic field.

Referring to FIGS. 1, 4 and 5 steps B1, B2, B3-$i$, B3-$ii$, B4, B5 of magnetic bead aggregation assay 110 are described. Step B6 which provides a detection step for characterisation of the aggregation state of the magnetic bead aggregation assay and is different for the different detection means or analysers of FIGS. 1B6 and FIG. 4B6 and FIG. 5B6.

Referring to B1, superparamagnetic particles 140 (SPM's) were either (i) purchased with a streptavidin monolayer or (ii) carboxyl beads were coated with PEG and conjugated to an antibody of choice. Referring to B2 superparamagnetic particles 140 are incubated with target 130/135. Referring to FIG. B3$i$ aggregation of the beads may be aided by the use of an aggregation means 160 comprising a magnetic field 165 as shown using the magpull processing step, as described in further detail below. Referring to FIG. 3B3-$ii$ it is noted that samples 130 may also be analysed without the application of the magnetic field. Referring to FIG. 3B4/B5 the beads may be washed and resuspended before analysis.

Referring to FIG. 4B6 the aggregation state of the SPMs 140 was determined and characterised using flow cytometry. The analysis step comprises measuring the bead aggregation or aggregates on an aggregate by aggregates basis or on a particle-by-particle basis. The characterization of the bead aggregation is based on using the physical properties of the bead aggregates, i.e., measuring magnetic moment (FNLM) or measuring volume (Flow cytometry (FC), FNLM) of the aggregates.

Referring to FIGS. 1, 4 and 5 examples of a method of analysis a sample using magnetic bead agglutination assay 110 using super-paramagnetic materials (SPM's) according to the present specification are described.

It will be appreciated that the specifics of the operation will depend on the assay time and bead concentrations. The aggregates 155 can be large and contain numerous super-paramagnetic materials (SPM's). See example aggregate FIG. 3C.

In the examples described which provide two initial starting particles 135 and 140 as exemplary of the type of analysis that may be conducted a number of steps are completed as part of a magnetic separation and labelling. This detail is exemplary of the type of analysis that may be conducted as part of the i1A steps of FIG. 4 as described above.

Steps of an assay method of the specification include the following:
step of attaching one or more antibodies or receptors of choice to magnetic (or nonmagnetic) beads
step of mixing the antibodies with sample analyte cells prior to attaching the magnetic beads to the cells using a protein or similar receptor, prior to introducing the sample comprising beads of a first and a second type, aggregating a plurality of beads
wherein aggregating a plurality of beads comprises the further steps of:
providing a container with a sample solution with beads in the presence of a magnetic field of a first orientation
allowing the beads to migrate to and collect on a side surface of the container;
exposing the beads to a magnetic field of a second orientation to allow formation of aggregates of the beads
subsequent to the collection of the beads on a side surface of the container, replacing the sample solution with a second solution and re-exposing the new solution to a magnetic field to allow the beads to migrate to and collect on the side surface of the container.

The beads 140 are super-paramagnetic beads. The method further provides for monitoring analyte induced aggregations or agglutinations 155 of magnetic beads using a suitable analyser or detector arrangement 200. For example, a suitable analyser includes a Flow cytometer 250 as described above with reference to FIGS. 4A to 4D. Further, as described above with reference to FIG. 1 a suitable analyser may comprise an F-NLM separator. The method and system of the present specification provides a magnetic bead aggregation assay platform for characterising bead aggregations. The analysis step comprises measuring the bead aggregates on an aggregate-by-aggregate basis. The characterization of the bead aggregation is based on using the physical properties of the bead aggregates, i.e., measuring magnetic moment (FNLM) or measuring volume (Flow cytometry (FC), FNLM).

As noted above, the method may further include transporting the magnetic bead aggregates from the reaction chamber to a detection means.

The assay system 100 advantageously provides high sensitivity for short reaction times. Further, as noted the system 100 and method provide that is not necessary to wash the beads 140 after reaction with the sample 130. Thus the system and method provide that the reaction can be forced or progressed forward beyond normal equilibrium.

Method of operation of magnetic bead agglutination assay is described in further detail with reference to examples of FIGS. 1, 4 and 5.

Step B1—SPM's are either (i)—purchased with a streptavidin functionality, or (ii) carboxyl beads from the same supplier are covered with a PEG coating that is later conjugated to the protein of choice.

Step B2—SPM's are incubated with target.

Step B3$i$—Aggregation of the beads is aided via the use of a "magpull" stage, or if required Step B3-$ii$ the sample can be analysed immediately by passing it downstream for further analysis.

Step B4—During the "magpull" stage the beads may be washed. Step B5—Beads are resuspended before analysis which will be conducted as part of a downstream analyser.

Step B6$i$—The aggregated particles are provided downstream to an analyser to allow for further analysis. This can be used to count the number of bead aggregates.

In the analysis step, the bead aggregates are monitored or measured on an aggregate by aggregate or particle by particle basis.

Detection/Analysis

Optical Detection for Example, Flow Cytometry

Particle aggregation measurements may be performed using a flow cytometry (FC) instrument with data analysis performed using suitable software. The sample is placed into the FC instrument and multiple events recorded. For example, the number of monomers—dimers etc may be counted by gating individual areas of the scatter plots. The use of flow cytometry (or the F-NLM detection) systems allows quantitative analysis of the particle aggregations for example counting of the percentage of monomers, dimers, trimers and tetramers etc formed in the MBA assay. The detection may be optical detection.

By way of illustration, the system of the specification not being limited thereto, a number of examples are described in more detail as well as a number of the steps of the method and further optional steps of the method, the present method and system of the specification not being limited thereto. In particular, exemplary assay systems 100 and methods according to the present specification are described where a magnetic bead aggregation assay 110 has been demonstrated for analytes 135 in a sample 130 for example, the model biotin-bovine serum albumin (BBSA) system and herpes simplex virus 1 and 2 (HSV-1 and 2) using flow cytometry, see examples 1 and 2.

Control of Aggregation

The method of the present specification further provides for controlling the aggregation of magnetic beads in the magnetic bead agglutination. Parameters that may be controlled to control the aggregation of superparamagnetic particles SPMs include the following:
bead concentration,
binding capacity,
reaction time, and
application of magnetic force (Magpull stage)

The magnetic aggregation assay 110 and system 100 is highly versatile being capable of using a widely used diagnostic platform namely, flow cytometry or other suitable diagnostic platform for example F-NLM separator and detection means, or NLM detector, or particle sizer detector.

The resulting assay platform 100 is capable of operating over six orders of magnitude of concentration with assay times as low as 5 minutes and sensitivities on the fM scale.

The sensitivity of the assay system 100 increases with the density and affinity of the receptors 145 on the beads 140, which is attributed to an increase in the rate of accumulation of the analyte on the SPMs 140.

The rate of aggregation of the beads 140 further increases with a decrease in the size of the beads. Thus the sensitivity also increases for smaller particles 140.

The rate of aggregation of the beads 140 further increases with an increase in the density of the beads (SPMs).

The rate of aggregation of the beads 140 further increases with the use of magnetic force as applied in the aggregation step. The rate of aggregation of the beads 140 increases with the MAGPULL step.

Increasing the reaction time results in an increase in the fraction of aggregates formed. For example, it was found that an increase in reaction time resulted in an increase in the fraction of dimers formed in the MBA assay 110 in the concentration range between 10-13 and 10-9 M.

Higher sensitivity is associated with the rapid onset of the hook effect due to the saturation of the receptors on the beads.

The system and method provides that aggregation of magnetic beads (SPMs) in the presence of an analyte can be tailored and predicted by controlling bead size and/or binding capacity and/or affinity, and/or bead concentration. The facility for control of the aggregation of the SPMs in the presence of a target produces a simple and sensitive analytical method.

Further, a factor for the improved sensitivity of the aggregation assays 110 is the ability to eliminate non-specific bead-bead interactions. Typically in the assays of the examples described, the fraction of beads present as a dimer in the absence of the analyte was approximately 8±4%. Whilst these dimers could be removed prior to the assay by placing the beads in a sonic bath, once the beads had undergone a magpull their inability to re-disperse resulted in a low but constant background signal. It is not only the beads themselves that can undergo non-specific interactions, high protein coverage on the beads can also lead to non-specific protein/bead and/or protein-protein interactions which can raise the level of the background aggregation.

Peg Modification

As noted above a high binding capacity provides an enhanced signal. However, binding capacity must be balanced against levels of background aggregation. Furthermore, as biological samples are complex matrices which include high concentrations of nucleic acids, lipids, carbohydrates and proteins that are potentially capable of binding non-specifically to the bead surface. To adapt the above assay 110 to be better suited for clinical samples, carboxyl coated beads may be provided modified with a protective PEG layer. Provision of a PEG layer reduces the amount of non-specific adsorption onto surfaces whilst helping disperse and solubilize the beads. Functional groups may be incorporated into the PEG layer, at a controlled ratio allowing conjugation to a defined number of proteins. A PEG coupling synthesis, outlined within the experimental section and shown schematically in FIG. 4A, was optimized by implementing a capping stage within the surface chemistry modification. Each stage of the surface modification can be monitored by measuring its surface zeta potential. Initially a negative carboxyl surface, curve 1 FIG. 6a, is modified to contain amine groups, curve 2, which are reacted with a PEG polymer, curve 3. Any unreacted amine groups are converted to hydroxyl groups as outlined above. This stage was found to help reduce the number of non-specific aggregates illustrated in FIG. 2Sb. Incorporating a mixed PEG functionality, ie. BOC terminated PEG's allowed for the streptavidin protein to be conjugated onto the beads surface. The PEG modification did not affect the aggregation behaviour of the beads.

It is noted that while a high binding capacity is needed for an enhanced signal, however, this must be balanced against levels of background aggregation.

Examples of the application and operation of the system and method of the present specification are provided. It will be appreciated that these examples are provided to assist in describing the invention. Some further features of the invention are described with reference to examples 1 and 2. The examples are not limiting of the system and method provided.

See for example, the streptavidin-biotin assay as described further below. The streptavidin-biotin interaction was used as an example as it is among the strongest known noncovalent specific molecular interactions, i.e., KD~10-15 M. Under the optimal assay conditions, the MBA-FC assay could be used to detect biotin across six orders of magnitude in concentration with sensitivities in the fM level, see the exemplary method of Example 1. The applicability of the MBA-FC assay for the detection of the HSV-1 and 2 viruses is described also, see Example 2.

The antibody-based assay highlighted the role of the binding target and affinity in the sensitivity of the MBA. Further by utilizing their magnetic properties in the presence of a magnetic field, the speed and sensitivity of an MBA assay can be increased. FIG. XX summarizes the influence of particle size, binding capacity, avidity/affinity and particle concentration on the sensitivity and onset of the hook effect for the MBA assay. In this section the chemical and physical factors that determine the response of the assay are described.

Table 1 summarizes the diffusion and convection rate constants of BBSA, HSV, and the beads. The relatively low diffusion rate constant of the beads means that the encounter rate of the beads would normally limit the overall rate of reaction, but the SPMs in the MBA assay being magnetically concentrated resulted in an increased speed of bead encounter.

Aggregation

It will be appreciated that the above steps comprise the sequential exposure of beads to magnetic fields of different orientations. In effect magnetic means 165 is operable to apply a magnetic field to the sample in the reaction chamber 120 subsequent to the step of reacting the sample with the magnetic beads. The magnetic field may comprise a magnetic field gradient or a time varying magnetic field. Effectively in the second step the relative orientation of the beads to the field is varied. This may be achieved through use of moving the beads relative to the magnetic field or maintaining the beads stationary and varying the direction of the applied field.

In step B3-i—the MagPull step, the sample was left in the presence of a magnetic field until all the beads were judged to have come out of solution (1 min), the initial solution was removed leaving all the beads on the side of the container and 500 µl PBS was added to the beads. The solution was stirred and the magnet was replaced and the beads separated out under the magnetic field for a second time. Once the SPMs had collected onto the side of the container the tube was rotated 90 degrees, whilst maintaining the magnetic field. This allowed the pellet of SPMs to roll over the side of the container and each other until they had settled over the magnet again, at this stage the magnet was removed and the pellet was allowed to settle to the bottom of the vial for 30 sec before finally being vortexed, resuspended and diluted into 1 ml of PBS for analysis. This process we term "Magpull" and is aimed to increase the particle-particle interactions and thus increase the number of particle aggregates.

In further analysis of the effect of the Magpull stage it is noted that after being incubated with the analyte for 30 min that the beads were close to being saturated. Further analysis indicated that this saturation most likely occurs within the first few minutes.

Indeed experimental data such as the data shows in FIG. 8, which shows Concentration of dimers in an assay as a function of analyte concentration, 1—30 min assay magpull, 2—5 min assay magpull, 3—5 min assay no magpull it is clear that only minor changes in the aggregates numbers are observed when the assay time is reduced. The fact that there exists a relatively low efficiency in relationship between aggregates and analyte concentration means that this technique provides a signal, over eight orders of magnitude.

The use of the magpull step to affect the number of dimers at longer hybridization times is minimum when the concentrations of analyte is high. The use of the magpull step is seen to cause an increase for formation of dimers at lower concentrations, curve 2—FIG. 14. The samples in some assays was analysed prior to the magpull step (curve 3—FIG. 14) similar curves are observed, however in these samples the number of dimers and larger aggregates depends upon the collision frequency of the beads in solution. At high concentrations the curves correlate with those of the magpull experiment, but the number of measured aggregates in the presence of the magpull was always greater Reaction/Aggregation FIG. 9 summarizes the influence of particle size, binding capacity, avidity/affinity and particle concentration on the sensitivity and the onset of the hook effect for the assay. In more detail, magnetic bead aggregation 155 as described above as provided in the magnetic bead agglutination assay 110 is the result of two reactions.

In the first reaction, the analyte 135 ($b$) reacts with the receptors 145 on the beads 140 (S) to produce the product 155 (B)

$$S + b \underset{k_{-1}}{\overset{k_1}{\rightleftharpoons}} B, \quad (1)$$

where $k_1$ and $k_{-1}$ are the forward and reverse rates of reaction, respectively.

The rate constants in this reaction result from the convective mass transport of the analyte 135 to the surface of the beads (h) and the reaction of the analyte 135 with the receptors 145 immobilized on the beads ($k_{S-b}$).

The second reaction involves the reaction of the analyte 135 on one bead 140 (B) with the receptor 145 on another bead 140 (S) to result in the formation of bead aggregates 155 (A)

$$B + S \underset{k_{-2}}{\overset{k_2}{\rightleftharpoons}} A, \quad (2)$$

where $k_2$ and $k_{-2}$ are the forward and reverse reaction rates of the beads, respectively. The rate constants in this reaction result from the rate of encounter of the beads and the reaction of the immobilized analyte and receptor ($k_{S-B}$).

Table 1 summarizes the diffusion and convection rate constants of BBSA, HSV, and the beads.

The super paramagnetic beads 140 in the magnetic bead agglutination assay 110 being magnetically concentrated result in an increased speed of bead encounter.

At low concentrations of analyte 135 the sensitivity of the magnetic bead agglutination assay 110 was determined by reaction (1). The concentration of bound analyte ($C_B$) can be predicted for a second-order reaction where $k_1 \gg k_{-1}$ to vary with time (t) as $$C_B = C_{b,o}\left[1 - \exp\left(-\frac{t}{\tau}\right)\right], \quad (3)$$

where $C_{b,o}$ is the initial concentration of analyte at the surface of the beads and $\tau$ is the time constant of the sigmoidal growth of $C_B$. The time constant

is a function of the initial concentration of receptors on the beads ($C_{S,o}$), the total surface area of the beads (a), and the total volume of reaction (V). Previous studies of the reaction of biotinylated proteins with 200 nm streptavidin SPMs confirmed the bound analyte concentration initially underwent exponential growth and $\tau$ has experimentally been shown to be linearly related to $C_{S,o}$. In the case of an exemplary arrangement of the present specification, the sensitivity of MBA assay increased with the density of streptavidin as shown in the apparent increase in sensitivity of curves 1 and 2 in FIG. 6A. Thus, the decrease in the magnitude of the maximum of curve 2 of FIG. 5 is associated with a decrease in $\tau$.

Reaction kinetic theory suggests that the rate of reaction of the analyte with the bead ($k_1$) is determined by the rate of mass transport of the analyte to the bead (h) and its reaction with the receptor ($k_{S-b}$), i.e.,

The relative importance of these parameters is defined by the second Damkohler number ($Da_{II}$), which has been presented as a function of receptor concentration in Table 2. The fact that $Da_{II} < 1$ over the range of receptor concentrations used in this study indicates that the overall rate constant was dominated by the reaction rate of the analyte with the receptors immobilized on the beads.

The parameters presented in Table 2 were calculated based on a reaction rate of $10^8$ $M^{-1}s^{-1}$, which is a rate characteristic of a diffusion limited, homogeneous protein reaction. SPR results for the HSV antibody-antigen interaction suggest that the on rate of the immobilized receptor reaction was $\sim 10^5$ $M^{-1}s^{-1}$. Thus, calculations of the time constant of the reaction, as summarized in Table 2, indicate it is of the order of 1,000-10,000 seconds for the 3 micron particle assays.

TABLE 1

Mass transfer parameters of the MBA assays.

|  | r (nm) | $D_r$ (1/s) [1] | D (m²/s)[2] | h (m/s) [3] |
|---|---|---|---|---|
| BBSA | 3 | $6.05 \times 10^6$ | $7.25 \times 10^{-11}$ |  |
| HSV | 10 | $1.63 \times 10^5$ | $2.18 \times 10^{-11}$ |  |
| Bead 1 μm | 500 | 1.30 | $4.35 \times 10^{-13}$ | $1.5 \times 10^{-4}$ |
| Bead 3 μm | 1,500 | 0.0484 | $1.45 \times 10^{-13}$ | $4.83 \times 10^{-5}$ |

[1] Rotational diffusion coefficient of a sphere $D_r = k_B T/8\pi\mu r^3$, where $k_B$ is Boltzmann's constant, T is temperature, μ is viscosity and r is the hydrodynamic radius.
[2] Diffusion coefficient of a sphere $D = k_B T/6\pi\mu r$.
[3] BBSA convection coefficient $h_1 = D/r$.

TABLE 2

Reaction rates and time constants of
the streptavidin-biotin MBA assay.

| Receptor concentration (M) | $Da_{II}$ [1] | $k_{S-b}$ (1/s) [2] | $k_{S-b}$ (m/s) [3] | τ (sec)[3] |
|---|---|---|---|---|
| $10^{-8}$ | 0.39 | 1 | $1.5 \times 10^{-6}$ | 780 |
| $10^{-9}$ | 0.039 | 0.1 | $1.5 \times 10^{-7}$ | 7,800 |
| $10^{-10}$ | 0.0039 | 0.01 | $1.5 \times 10^{-8}$ | 78,000 |

Second Damkohler number $Da_{II} = kC_o^{n-1}L^2/D$, where k is the reaction rate, $C_o$ is the initial concentration of the ligand, L is a critical dimension (1.5 microns), and n is the order of the reaction. The $Da_{II}$ was calculated based on a streptavidin-BBSA reaction rate of $k_{S-b}$ of $10^8$ M$^{-1}$s$^{-1}$, which is the upper limit for diffusion limited, homogeneous protein reaction. $k_{S-b}$ is the reaction rate of free BBSA with strepavidin on the bead for a defined concentration of streptavidin. $k_{S-b}$ is the reaction rate expressed in term of a surface concentration. τ has been calculated for 50 fM of 3 micron beads.

TABLE 3

Kinetics for immobilized HSV-1-antigen binding interactions
as determined by the Biacore technology. Antigen was immobilised
onto the surface, monoclonal, mAB, and polyclonal, pAB,
antibodies injected for analysis.

|  | $k_{on}$ (M$^{-1}$·s$^{-1}$) | $k_{off}$(s$^{-1}$) | $K_D$ (M) |
|---|---|---|---|
| pAb | $4.71 \times 10^4$ | $2.24 \times 10^{-2}$ | $2.64 \times 10^{-7}$ |
| mAb | $8.10 \times 10^4$ | $5.13 \times 10^{-3}$ | $6.33 \times 10^{-8}$ |

The relationship between the bead aggregation and analyte concentration has been defined as the efficiency. A 100% efficiency arises from a 1:1 relationship between dimers and the target analyte, i.e., a reaction with 100% efficiency would produce 50 dimers in a sample of 50 analytes per ml. Efficiencies as high as 70% have been achieved for beads with diameters between 20 and 200 nm. In this study, 50 fM of 3 μm diameter SPMs were used that had a total streptavidin concentration of 75 nM. The MBA-BBSA reaction efficiency was significantly less than 1%, which appears to be a characteristic of the longer time constants and lower rotational mobility of the larger beads used in this study.

Example 1—Detection of Strepavidin
Functionalised SPMS Added to Solution Containing
BBSA Using a System and Method According to
the Present Specification Materials The particles used in this example assay according to an assay system and method of the specification were, Dynal particles carboxyl (1 micron—650.12 and 3 micron—143.05 D), and streptavidin coated (1 micron—650.01 and 3 micron—653.05) Invitrogen. The streptavidin beads were used as delivered, however, the carboxyl beads were modified with a PEG layer described below. BOC-NH-PEG-NHS MW 3000, and CH30-PEG-NHS MW 2000 was purchased from Rapp Polymere, Germany. All chemicals and proteins were used as purchased without further purification. Commercial particles for analysis were first collected with a magnet before being washed three times in the reaction buffer prior to use. Buffers used PBS (0.01 M phosphate buffer, 0.0027 M Potassium Chloride and 0.137 M Sodium Chloride, pH 7.4), PBST (PBS with 0.05 (v/v) % Tween). Carbonate buffer (50 mM Sodium carbonate, pH 8.2), Carbonate buffer-PEI solution (50 mM Sodium carbonate, pH 8.2, 5% wt/wt, PEI), Carbonate buffer-PEG solution (50 mM Sodium carbonate, pH 8.2, 0.6M Potassium sulphate), MES buffer (50 mM MES, pH 6.0). All separations were performed using a Dynamag separator. Bovine serum albumin, BSA, Dimethyl sulfoxide, DMSO, Polyethylenimine 50 wt. % (MW 1300), Potassium Carbonate, 2-(N-Morpholino) ethanesulfonic acid (MES), 2-Mercaptoethanol, BME, Potassium sulphate, Sodium Dodecylsulphate, SDS, Trifluoroacetic acid, Tween-20, were all purchased from Sigma Aldrich. 1 step ABTS solution, biotin-HRP, Biotin-BSA, BBSA, 1-Ethyl-3-[3-dimethylaminopropyl]carbodiimide hydrochloride, EDC, Excellulose Desalting Columns, Fetal bovine serum, Sulfon-hydroxylsucciminide, N-hydroxysulfosuccinimide, sulfo-NHS and, N-Succinimidyl S-Acetylthioacetate, SATA and Sulfosuccinimidyl 4-[N-maleimidomethyl]cyclohexane-1-carboxylate, SMCC, and Streptavidin, were purchased from Thermo Scientific.

Surface Chemistry Modification.

Initially the beads were purchased with a carboxyl surface chemistry, FIG. 3, A1 Stage 1—Amine modification. 1 ml of carboxyl coated beads (5 mg/ml) were washed (×3) with MES buffer. The beads were then sonicated, before a solution of 5 mg EDC, and 5 mg sulfo-NHS, in 0.5 ml MES buffer, was added. The beads were incubated at room temperature, RT, on a rotating wheel for 30 mins yielding NHS activated beads. The beads were collected with a magnet and washed (×2) with carbonate buffer (pH 8.0), before adding 1 ml of 5% PEI solution. The particles were sonicated, before placing them on a rotating wheel at RT for 2 hours, before being washed with carbonate buffer. Stage 2—Surface modification with Polyethyleneglycol, PEG. 1 ml of PEG solution (BOC-NH-PEG-NHS and mPEG-NHS in carbonate buffer with K2SO4 0.6M) was added to 1 ml amine modified beads. The addition of amine group via the deprotected BOC-NH-PEG allowed conjugation to proteins. By varying the ratio of BOG-PEG: MPEG the total number of conjugation points and thus the binding capacity could be controlled. The beads were sonicated before being incubated at 50° C. for 2 hrs. Stage 3—Capping of reactive amine groups. To remove any unreacted amine groups from the underlying PEI layer the beads were first washed with PBST (×3). SMCC was dissolved into DMSO at 20 mg/ml immediately prior to use and diluted to 1 mg/ml with PBST before being added to the freshly washed beads. After 60 mins the beads were washed (×2) with PBST before a 1 ml solution of PBS containing 2% (V/V) mercaptoethanol. The beads were incubated with the BME solution for 2 hours, after which the beads were washed (×5) with PBST. This stage capped the unreacted amine groups, this capping stage had the effect of lowering the residual zeta potential, FIG. 10. Stage 4—Coupling Protein to modified PEG surface. The conjugation of proteins to the free amine on the beads was done by first modifying the proteins with a —SH group via SATA chemistry, after the proteins were labeled with a SATA functional group they were coupled to the beads using the SMCC coupling chemistry.

Assay Format

The SPMs (5 mg/ml) were routinely stored in PBST buffer containing 0.1 (wt/wt %) BSA. This storage served to act as a blocking solution reducing non-specific adsorption. When required the SPMs were diluted to the required concentration, and sonicated briefly (<10 sec). Typical assay volumes were ~500-1000 µl. The final dilution of the beads and its resultant concentration is reported in all graphs and calculations. Samples were either prepared by diluting the target biotinylated-BSA into PBST. The solution was incubated at room temperature on a rotating wheel allowing end-over-end mixing. After the required hybridization time, the sample was either diluted with PBS buffer and FIG. B1, 3ii, or subject to the magnetic assisted aggregation or "magpull", FIG. B1, 4.

Magnetic assisted aggregation—For the magpull—the sample was placed next to a magnet, with a field strength of 2.5 KGauss on its surface, until all the beads were judged to have come out of solution ~1 min. The initial solution was removed leaving all the beads on the side of the container and 500 µl PBS was added to the beads. The solution was stirred and the magnet was replaced separating the beads for a second time. Once the SPMs had collected onto the side of the container the tube was rotated 90 degrees, whilst maintaining the magnetic field. This allowed the pellet of SPMs to roll over the side of the container and each other until they had settled over the magnet again and at this stage the magnet was removed and the pellet allowed to settle to the bottom of the vial for 30 sec before finally being vortexed, resuspended and diluted into 1 ml of PBS for analysis. "Magpull" is aimed to increase particle-particle interactions and thus increase the number of particle aggregates. Bead aliquots were added to a solution containing the target and the concentration of beads was calculated based upon this final dilution.

Method of Detection Using Flow Cytometry and Characterisation of Sample and Discussion of Results and Features Flow cytometry Particle aggregation measurements were performed using flow cytometry (FC) instrument with data analysis performed using suitable software.

The sample was placed into the FC instrument and 100,000 events recorded.

The number of monomers—dimers etc was counted by gating individual areas of the scatter plots shown in FIG. 4D, FIG. 6A. Each assay was run in triplicate and the average values are plotted in all graphs. A blank background scan was also performed to show the beads did not aggregate nonspecifically in the presence of the magnetic field. Typically in such experiments the number of aggregates was <10% of the beads counted.

Particle Characterization

All zeta potential measurements were performed using a Zetasizer Nano ZS, using the DTS-1060 cells. 20 µl of particles at 1 mg/ml, were placed into a 1.5 ml centrifuge tube and washed three times with 1 ml solution of 1 mM KCl solution at the required pH, before being suspended in appropriate buffer and pH.

Protein Coverage of Beads.

The biotin binding capacity all beads were done using the standard biotin-HRP and ABTS quantification Detection of Biotinylated BSA with MBA-FC FIG. 4 illustrates the stages in the MBA-FC assay, in the first step, FIG. 4B2, streptavidin functionalized SPMs are added to a solution containing BBSA, each BSA protein contains an average of 9 biotin molecules per BSA protein (data from supplier). The SPM's for MBA-FC need to be highly uniform in diameter as this makes the FC signal from the aggregates easy to identify. In this study, commercial Dynal beads were used as they have a relatively uniform size, i.e., <2% coefficient of variation, CV, FIG. 10, and a number of particle sizes are available, i.e., 1 and 3 µm. In the second step, shown in FIGS. 4 B3 to B5, a magnetic gradient was applied to the bead suspensions to separate the beads and accelerate the rate of bead interaction with each other. In the final step, shown in FIG. 4B6, the SPM aggregation state was determined by Flow cytometry. As an example of achievable runtime, it is noted that the magnetic separation procedure, steps 4B-3 to 4 B-5, took approximately 3 minutes to complete and the flow cytometry analysis was completed in approximately 5 minutes.

Referring to FIG. 4D the flow cytometry (FC) analysis of 100,000 particles for MBA assays over six orders of magnitude of BBSA concentration for 3 µm streptavidin functionalized beads is described.

The x-axis of these figures presents forward scatter intensity, which is characteristic of bead size, and the y-axis presents side scatter intensity at 488 and 635 nm. The fluorescence in the side-scatter signal was produced by the auto-fluorescence of the SPMs. The fluorescence signal was not required to complete these measurement but fluorescent markers could easily be employed to aid the analysis in the case in which multiple analytes are being simultaneously measured. The FC signals shift towards higher forward and side scattering in the presence of BBSA, which is a characteristic of bead aggregation. Three other trends can be observed in these results, as follows:

First, the presence of a large cluster of data points that represents the individual beads, or monomers, was present in the bottom, left corner of all plots. This feature is confirmed when a sample of beads without the addition of an analyte is passed through the FC (FIG. 11).

Second, the narrow size distribution of the SPMs resulted in tightly packed clusters of data points making the numbers of specific aggregates relatively easy to identify, as defined by the boxes delineated by dashed lines in FIG. 4D.

Third, all cluster populations were observed to increase as the concentration of BBSA was increased from $3 \times 10^{-14}$ to 3 nM. However, at 300 nM BBSA the number of clusters was observed to decrease.

Referring to FIG. 6A the quantitative analysis of the percentage of monomers, dimers, trimers and tetramers formed in the MBA assay using the 3 µm beads, as a function of BBSA concentration is described.

Conservation of the total number of SPMs meant that the formation of aggregates was closely correlated with the decrease in monomers, i.e., the minimum number of monomers appeared at a BBSA concentration at which the maximum number of dimers, trimers, and tetramers were observed. At concentrations between $10^{-15}$ and $10^{-9}$ M there was a direct correlation between the number of dimer aggregates and the BBSA concentration. At concentrations of BBSA greater than 1 nM there was a sharp decrease in number of all forms of aggregates and increase in monomers was observed.

The decrease in signal from aggregation at high concentrations of analytes has been well document for agglutination assays. It results from the saturation of the particle surface with analyte and is known as the 'hook' effect.

It is also clear that a significant numbers of trimer and tetramer aggregates form at $10^{-8}$ M BBSA, which appears to be characteristic of the higher coverage of biotin on the beads.

Influence of reaction time and magnetic force on the MBA assay sensitivity

FIG. 6B presents the number of dimers formed as a function of BBSA concentration, reaction time, and magnetic field. Several observations can be made from these results.

First, increasing the reaction time to 30 mins from 5, curves 1 and 2 respectively, resulted in a significant increase in the fraction of dimers formed in the MBA assay in the concentration range between 10-13 and 10-9 M. The 30 minute assay results presented in curve 1 demonstrate an increase in aggregation over the background signal at concentrations as low as 10-13 M. Whereas the lowest concentration signal that can be observed in the 5 minute assay in curve 2 was 10-11 M.

Second, application of magnetic force to the SPMs resulted in an increase in the number of aggregates formed across the range of concentrations studied by approximately 1-5%.

According the method provides that the relevant time scale for the formation of aggregates is the result of at least three factors, i.e., the rate of the reaction of BBSA with the streptavidin on the beads, the convective mass transport to the BBSA to the SPMs, and the reaction of the SPMs with each other to form aggregates.

Thus, the convective transport of BBSA to the microparticles was the rate-limiting step that determined the coverage biotin on the SPMs. The diffusion and convection coefficients of a 3 μm diameter bead are 1.5×10-8 cm2/s and 2.9×10-6 cm/s, respectively. Thus, the time scale for the BBSA transport to the microparticle was 600 seconds for a particle density of 6.25×107 per milliliter, which is equivalent to 50 fM of beads. Thus, the relevant time scale for the reaction was 10 minutes. The increase in the sensitivity of the assay for the 30 minute reaction time can thus be linked to the convective transport of BBSA. The convective time constant can be decreased by increasing the convention coefficient or decreasing the characteristic length scale. This can be achieved by using smaller particles or higher densities of particles, respectively.

The relationship between the bead aggregation and analyte concentration has been defined as the efficiency. A 100% efficiency arises from a 1:1 relationship between dimers and target analyte, i.e., a reaction with 100% efficiency would produce 50 dimers in a sample of 50 analytes per ml. Efficiencies as high as 70% have been achieved for beads with diameters between 20 and 200 nm. In the exemplary method, 50 fM of 3 μm diameter SPMs were used that had a total streptavidin concentration of 75 nM. The MBA BBSA reaction efficiency here was significantly less than 1%. These relatively low reaction efficiencies appear to be a characteristic of the larger beads used in this study. The rotational diffusion coefficient scales as [rh]-2 and thus 3 μm bead spontaneously rotate at a rate 225 times slower that a 200 nm bead. The larger beads will therefore have a higher steric factor to overcome for the alignment of the capture probe and target.

The Influence of Magnetic Forces on the Assay was Determined by Analyzing Aggregate Formation with and without Magnet Field.

Curves 2 and 3 in FIG. 6B, have a similar form at high concentrations of analyte the curves, but at lower analyte concentrations the number of measured aggregates in the presence of the magpull was always greater, demonstrating the enhancement of the aggregation. It was striking, however, that there a relatively low efficiency for dimer formation still exists, which suggests that the reaction of the biotin immobilized on the 3 μm SPMs was not very efficient. The low efficiency of the assay clearly limits the sensitivity of the assay but also means that MBA assay provides a signal over six orders of magnitude.

Influence of bead concentration, size, binding capacity and diameter on the response of MBA To further demonstrate the sensitivity, dynamic range, and hook effect of the MBA assay, a set of experiments were devised in which the binding capacity and bead concentration were systemically varied. FIG. 6C presents the percentage of dimers and monomers produced by the reaction of 3 μm SPMs with BBSA at concentrations ranging between 10-14 and 10-6 M for 30 min. Curves 1 and 2 present the results for a SPM bead concentration of 50 fM with streptavidin coverages of 2×106 and 2×105 molecules per bead, respectively. Curve 3 presents the results for a SPM bead concentration of 5 fM and streptavidin coverage of 2×106 molecules per bead. Three observations can be made about these results.

First, decreasing the concentration of streptavidin density on the beads resulted in a significant decrease in the fraction of dimers formed at a given BBSA concentration. This resulted in a corresponding decrease in sensitivity for the lower coverage beads.

Second, decreasing the number of beads whilst maintaining a higher streptavidin coverage resulted in a higher sensitivity of the assay, inferred from a higher number of aggregates at lower analyte concentrations, but also an earlier on-set off the hook effect.

Third, decreasing the number of beads did not decrease the sensitivity of the assay, which confirms that the rate of convective transport of BBSA to the beads is not the rate limiting step in the formation of dimmers.

The onset of the hook effect was found to be closely linked to both the concentration of streptavidin in the reaction and the density of streptavidin on the beads in the reactions in FIG. 6C. In each reaction the maximum number of dimers formed for a BBSA concentration, was just under the streptavidin binding capacity on the beads. This was to be expected, as the maximum number of dimers should occur just before the BBSA saturates the streptavidin sites on the beads. However, the exact ratio at which the BBSA saturates streptavidin appears to be dependent on the density of streptavidin on the beads. For the high streptavidin coverage, which was close to a monolayer, the BBSA appears to start to saturate the streptavidin when it exceeds 10% of the streptavidin concentration. At submonolayer coverage's of streptavidin, however, it appears the BBSA has to almost equal the streptavidin concentration before the surface is saturated.

To test the effect of particle size a similar set of experiments were then performed with BBSA for streptavidin functionalized 1 μm beads and the results are shown in FIG. 7. Qualitatively similar trends were observed, i.e., both the intensity and position of the maximum number of aggregates can be tailored by changing the bead number and binding capacity. Quantitatively, however, the results for the 1 μm beads differed from the 3 μm beads. It is clear from FIG. 7 that when a similar concentration of beads is used the peak in aggregation appeared at much lower BBSA concentration for the 1 micron beads and a much larger of fraction of beads formed aggregates (curve 1 in FIG. 6C and curve 2 6C show similar bead concentration for different particle sizes). The interpretation of this result is that when the same number of 1 and 3 μm beads are used the 1 μm beads aggregate more efficiently. This is due to the fact that the 1 μm beads have a higher rotational diffusion coefficient.

Another interesting deviation in the behaviour of the 1 μm compared to the 3 μm beads arises in the fact that the tetramers behave in a comparable manner to that of the monomers, i.e. the peak in tetramer concentration best matches the dip in monomers, FIG. 7A. It is not immediately clear why there should be a preference for tetramers during the MBA stage, when the 1 μm beads were run without the MBA, the peak in dimers best mirrored the monomer behavior, FIG. 7B. One possible explanation is that the 1 μm beads have a rougher surface morphology, FIG. S1, and when forced into contact under the influence of a magnetic field, vacant binding sites within the crevices bind to the BBSA leading to the formation of larger aggregates. The key factors that influence the aggregation of the beads and the onset of the hook effect are summarized in FIG. 8.

PEG-SA Modified Beads

A critical factor for the sensitivity of the aggregation assays is the ability to eliminate non-specific bead-bead interactions.

Typically in the assays above, the fraction of beads that was present as a dimer in the absence of the analyte was approximately 8±4%. Whilst these dimers could be removed prior to the assay by placing the beads in a sonic bath, once the beads had undergone a magpull their inability to re-disperse resulted in a low but constant background signal. It is not only the beads themselves that can undergo non-specific interactions, high protein coverage on the beads can also lead to non-specific protein/bead and/or protein-protein interactions which can raise the level of the background aggregation.

The experiments above highlight that a high binding capacity is needed for an enhanced signal, however, this must be balanced against levels of background aggregation. Furthermore, biological samples are complex matrices which include high concentrations of nucleic acids, lipids, carbohydrates and proteins that are potentially capable of binding non-specifically to the beads surface.

To adapt the above assay to be better suited for future clinical samples, carboxyl coated beads were modified with a protective PEG layer. PEG layer is provided to reduce the amount of non-specific adsorption onto surfaces whilst helping disperse and solubilize the beads. Functional groups can be incorporated into the PEG layer, at a controlled ratio allowing conjugation to a defined number of proteins.

A PEG coupling synthesis, outlined within the experimental section and shown schematically in FIG. 4A, was optimized by implementing a capping stage within the surface chemistry modification. Each stage of the surface modification can be monitored by measuring its surface zeta potential. Initially a negative carboxyl surface, curve 1 FIG. 6a, is modified to contain amine groups, curve 2, which are reacted with a PEG polymer, curve 3. Any unreacted amine groups are converted to hydroxyl groups as outlined above. This stage was found to help reduce the number of non-specific aggregates illustrated in FIG. 2Sb. Incorporating a mixed PEG functionality, ie. BOC terminated PEG's allowed for the streptavidin protein to be conjugated onto the beads surface.

The model streptavidin-biotin system was again chosen to demonstrate the PEG modification did not affect the aggregation behaviour of the beads.

The 3 μm binding curves are shown in FIG. 5, panel B. By using a binding capacity of approx 0.35 μg protein/mg of beads (a reduction of around 20% from the commercial beads), we were still able to observe a significant number of aggregates in the presence of the analyte. By lowering the binding capacity, and in conjunction with the PEG chemistry, we observed a reduction in the numbers of background aggregates to below <3±2%.

Variables in designing a magnetic aggregation assay and demonstrated its applicability using readily available commercial chemicals on a widely used diagnostic platform.

Factors which may be controlled to influence the sensitivity of the assay as shown in FIG. 9.

The bead-bead reaction is the rate-limiting factor determining the number of aggregates formed and thus the sensitivity and response-time of the assay.

This is somewhat surprising as the particles are forced into direct contact by the MBA assay and thus one would predict that the rates of reaction would be accelerated.

However, this is consistent with previous studies of micron size SPMs reacting with planar surfaces. In these single molecules measurements of the protein A-IgG interaction single molecule bonds were only observed to form after approximately 100 potential protein A-IgG interactions were allowed to interact with each other for 10's of seconds.

The resulting assay platform is capable of operating over six orders of magnitude of concentration with assay times as low as 5 minutes with sensitivities on the fM scale.

The sensitivity of the assay could be increased by increasing the density of receptors on the beads, decreasing the size of the beads used, and decreasing the total number of beads used in the assay. However, higher sensitivities sometimes resulted in a more rapid the saturation of the beads with analyte and thus earlier onset of the hook effect. Thus, by controlling the particle size, binding capacity, avidity/affinity, and particle concentration, the aggregation of SPM's in the presence of the target analyte can be tailored and predicted producing a simple and sensitive analytical method.

Example 2—MBA-FC for Detection of HSV-1 and 2

We have demonstrated the clinical applicability of this technique by detecting HSV-1 and 2. Prior to an antibody being immobilized on PEG modified beads, a series of control assays using the BBSA-Streptavidin system were first performed, as in FIG. 13. These confirmed that the PEG modifications did not cause the aggregation behavior to deviate from the previous experiments shown in FIG. 7. Initially, a polyclonal antibody was evaluated for the HSV-2 capture experiment, however, increased particle aggregation in the presence of the analyte was not observed (see FIG. 14). After switching to commercially available monoclonal antibodies, a clearer signal was created, but only in the presence of magnetic field, shown in FIG. 14, again demonstrating the benefit of using SPMs in conjunction with the MBA. Binding constants for the HSV-1 monoclonal and polyclonal antibodies were measured via SPR and the on-rates of the antibodies were very similar (data shown in Table 3). However, the off-rates for the polyclonal was ~5 times faster than the monoclonal antibody. This may have resulted in the dispersion of the aggregates in the ~2 minutes that elapsed from the execution of the MBA assay to running the sample in the FC for the polyclonal system. As such, we used monoclonal antibodies throughout the remaining experiments.

A typical response from the 3 micron beads for the detection of HSV-2 is shown in FIG. 8A. As the target antigen concentration increased, the number of monomers decreased and the number of dimers, trimers and tetramers increased. Three observations can be made about the antibody results. First, a hook effect was not observed in the results. Second, the monomer binding response was very broad, occurring across six-orders of magnitude in virus concentration from 10-12 to 10-6 M. The behaviour of the antibody assay highlights another key parameter that must be considered when designing aggregation assays, namely the affinity of the capture antibody with the target.

Various alternative arrangements of the device and system have been described. It will be appreciated that the device and system may be provided or manufactured in various configurations without departing from the scope of the invention. For example, the detector, monitoring and sensor means may be provided integrated into a single chip device or for connection in series. For example, components of the device or system may be provided as sterile or single-use or disposable components while other components may be provided for re-use, as required.

Referring to FIG. 17, as noted above the assay may also be analysed using a detection means comprising for example a pore detector.

FIG. 17 shows the sensitivity of the bead agglutination assay for both the nanorod and bead assays 110. The beads are commercially available MyOne superparamagnetic particles made by Dynal (Invitrogen) that are coated with streptavidin. The assay was performed by reacting the beads with a biotinylated aptamer that specifically reacts with the analyte, which was the well known biomarker PDGF. The biotin attaches the aptamer to the beads very strongly and results in a surface that can react with PDGF. The graph on the left shows the change in current as the particle moved through the pore—red and yellow for rods (CURVES 2 AND 3) and green (CURVE 2) for beads. The size of the aggregates clearly increased as the concentration of analyte was added increased for the rods and beads. The sensitivity of the assay for the beads was not as high as the rods but it still was possible to measure the presence of PDGF at 10 pM concentration for the beads. The FWHM signal (graph on the right) was weaker for the beads (CURVE 1) as they do not form long chains.

The results of a control assay and demonstration are also noted with reference to FIG. 10. In this example method, the Ni segments were modified with a fluorescent dye. Imaging confirm the localisation of the signal, and again and shows that the capture ligand/protein was only present on the Ni segment. A first control assay was done using the avidin-biotin system. Biotinylated BSA was captured from solution and caused the rods to aggregate. By controlling where the avidin is situated on the rods i.e. where the Ni segment is situated, it is possible to change the predicted response in the Izon detector. When the Ni segment was located in the middle of the rods end-on-end aggregation was not possible and hence only an increase in size is observed. When the Ni segment was located on the end of the rod both size it was noted that FWHM increased with analyte concentration. This was demonstrated again with the detection of biomarkers PDGF. Aptamers to PDGF can be found in literature by placing them onto the Ni segment the rods were caused to aggregate end-on-end. To show and compare the results using a 1 micron sphere, using the same target and aptamer. The size and FWHM for the spherical bead assay are also shown.

Figure 16A:
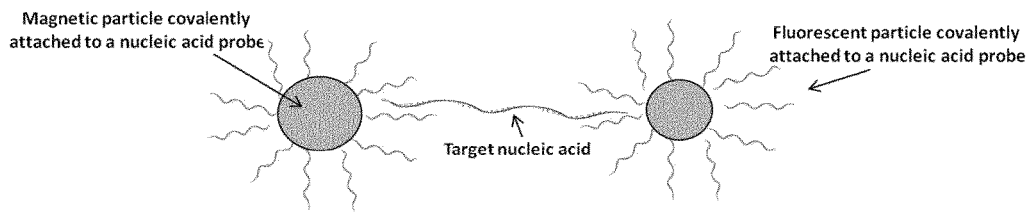
Figure 16B:
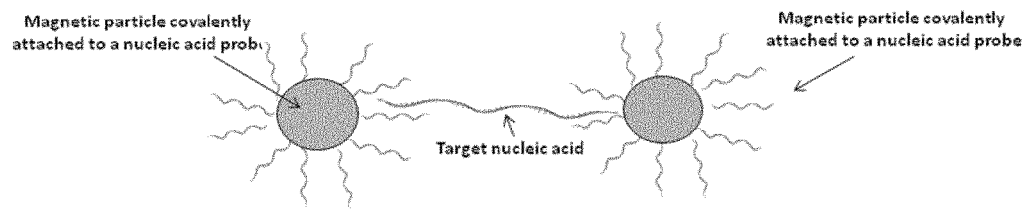
Figure 16C:
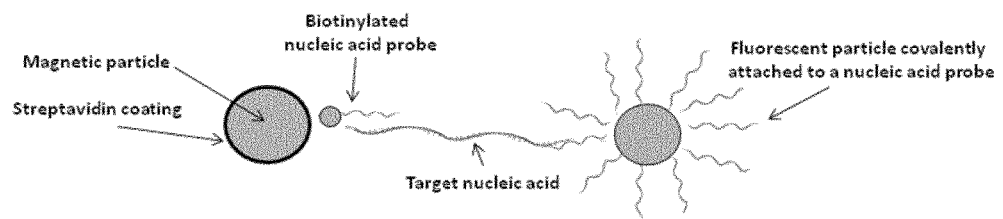

FIGS. 16a, 16b and 16c show examples of particles that can be analysed using a system in accordance with the present teaching. In the examples, the particle assembly is via nucleic acid interactions with subsequent detection.

In the arrangement of FIG. 16a, magnetic particles covalently attached to a nucleic acid probe form complexes with a second fluorescent particle also covalently attached to a nucleic acid probe. In FIG. 16b, a similar arrangement is provided however a second magnetic particle as opposed to a fluorescent particle is covalently attached to a nucleic acid probe. In FIG. 16c, an example of a streptavidin coated magnetic particle is coupled to a biotinylated nucleic acid probe forming complexes with a second fluorescent (which similarly to FIG. 16b could also be a magnetic particle) also covalently attached to a nucleic acid probe. It will be appreciated that in each of these configurations:

The magnetic and fluorescent particles can be of any size
The fluorescent particles can be of any fluorescence
The nucleic acid probes can be DNA or RNA
The nucleic acid probes can contain degenerate bases
The nucleic acid probes can be of varying length
The nucleic acid probe can contain any ligand complementary to the surface of the magnetic or fluorescent particles.

Advantages

The system and method of the present specification provides for analysing the agglutination and measuring indicators of agglutination properties and parameters. In particular the system and method provides an analysis step comprises measuring the bead aggregation on a particle-by-particle basis. The characterization of the bead aggregation is based on using the physical properties of the bead aggregation, i.e., measuring magnetic moment (FNLM) or measuring volume (Flow cytometry (FC), FNLM). The analysis provides an indication of the presence of bound complexes and further provides for quantitatively measuring combinations of magnetic particles combined with analytes.

It will be appreciated that the system and methodology described heretofore has a number of advantages over prior art techniques. The system and methodology is also simplified in comparison with the prior art approaches.

Using f-NLM detection means, the device, system and method of the present specification provide for frequency dependent separation which may be easily integrated and implemented in a digital arrangement. This provides a two tier system and method for the separation of beads based on their physical properties.

It will be appreciated that the magnetic bead agglutination assay may also be used with one or more detectors for use in providing analysis of the agglutinated beads. One example of such a detector is a fluorescent detector which may be usefully employed where the particles being detected are fluorescently tagged or otherwise luminesce on excitation. There is further provided a system and method using a magnetic bead assay for rare cell-virus separation for diagnostic purposes. Such a system and methodology may use small magnetic particles and a direct protein configuration. Preferably the method comprises the step of attaching one or more antibodies or receptors of choice to magnetic or nonmagnetic particles. The method may further comprise the step of mixing the antibodies with the cells prior to attaching the magnetic particles to the cells using a protein or similar receptor. In a preferred embodiment the method further comprises the step of aggregating particles prior to the step detection to drive the clustering of magnetic particles around the cells. Preferably the method comprises the step of attaching one or more antibodies, receptors, or DNA oligonucleotides to magnetic particles.

In this way the present teaching may be employed to rapidly separate multiple analytes bound to super-paramagnetic beads from milliliter volume samples. The method and system described provides for multiple sensing and is easily integrated with automatic control system to provide high levels of flexibility of application. The system advantageously provides for separation of multiple analytes such as for example, for separation/detection of analytes attached with particles, such as macro-organism, DNA, antibodies.

The magnetic bead aggregation assay system uses superparamagnetic microbeads (SPMs) to capture, purify, and detect an analyte. The assay system is advantageously rapid, sensitive and label-free, making it ideal for point-of-care testing.

The specification also provides a method of analyzing the magnetic bead aggregation (MBA) state using flow cytometry (FC). It will be appreciated that the magnetic bead aggregation state may also be measured using an alternative suitable detection means, being a detection means configured for monitoring on an aggregate by aggregate or particle by particle basis for example. The specification further provides a point of care testing device and method. The testing device can applied to a range of diseases but some of these technologies are limited by turnaround time, specificity, sensitivity, and cost. The assay system and super paramagnetic beads and method of the present specification provide an efficient and cost effective way to separate and pre-concentrate analytes from solutions helping to simplify the front-end of an assay.

Further advantages of the system, method and superparamagnetic microbeads of the present specification include the following: They are readily available through numerous commercial sources and synthesis strategies, offering a range of surface chemistries that can be quickly conjugated to any capture probe of interest. SPMs have already demonstrated their versatility for use in conjunction with techniques such as the polymerase chain reaction, mass spectroscopy and high-throughput linear magnetophoresis (LM) assay. Detection of the analyte in LM assays can be performed by characterizing the physical properties of the magnetic beads in the presence of the target producing a "label-free" detection platform.

In a preferred example of the system and method flow cytometry analytical technology is used for detection. Flow Cytometry has the ability to be miniaturized to small bench top systems, and offers continuous throughput of samples and multiplexing of analytes. For example, Flow cytometry technology may be provided capable of detecting up to 100 analytes at a time. Further FC can be easily modified in research laboratories using a range of fluorescent probes and nanoparticles, e.g., the use of quantum dots for the detection of multiple biomarkers.

The present method and system as described provides a magnetic particle aggregation assay and means for analysing the aggregates on an aggregate by aggregate basis using various alternative analysis systems or detection systems. The analysis is provided by analysis means or detection means configured to analyse the aggregates for example by measuring a physical property thereof. As noted the aggregates are analysed on the basis of physical properties of the aggregates. The aggregates provided by the aggregation method are of unspecified length or shape, being aggregates of magnetic beads. The aggregates are of identifiable form in a sample. Example, aggregates forms are shown with reference to FIG. 4C or FIGS. 3A-3C.

In a further method and system, the present specification provides a further approach to analysis of aggregations of magnetic particles as follows:

Referring to FIGS. 18 to 25, the present system and method provides a method for the detection of the analytes based on the use of nanoparticles which are configured for controlled aggregation with analytes to form complexes of different shape and/or size. The present specification also provides a multiplex method for the detection of analytes, based on the analyte induced nanoparticle aggregation.

Referring to the drawings and initially in particular to FIG. 18 exemplary nanoparticles 1 according to the invention are described. Nanoparticles 1 comprise a capture probe 2 for capture of an analyte 3. The particles 1 are configured to aggregate in a controlled manner with analyte 3 to form complexes or aggregates of different size and/or shape the resulting complexes or aggregates being detectable using a suitable detection system. The capture probe 2 acts as the centre for controlled aggregation of the nanoparticles 1 with analyte 3. By controlling the surface chemistry of the particles 1 during manufacture and in particular the location of the capture probe 2 thereon, the particles 1 may be configured to form aggregates of different shape and/or size, as required upon addition of analyte 3. It is accordingly possible to monitor the concentration of an analyte 3 in a sample by monitoring the changes in particle size or/and shape in a sample upon addition of nanoparticles 1. A count of the particles and/or aggregates provides information concentration.

Based on the aggregation method described above with reference to FIGS. 1 to 5, it is noted that the magnetic particles may comprise superparamagnetic beads and that aggregates having detectable physical properties are formed in an aggregating step. The aggregating step may be in the presence of a magnetic field.

The nanoparticles 1 comprise rod shaped particles. Rod shaped particles 1 are effectively configured to aggregate at different orientations depending on the location of the capture probe 2 thereon. Referring to FIG. 18 two alternative orientations of nanoparticles 1 aggregated with an analyte 3 are shown. The nanoparticles may be configured to aggregate end to end with analyte (as illustrated in FIG. 18B) to form a complex or aggregate 5 of greater length, or side by side with an analyte to form a complex or aggregate 4 of greater size or width (as illustrated in FIG. 18A).

The term rod shaped particles has been used herein to generally describe the particles with dimensions having aspect ratio greater than 1, it will be appreciated that particles of different suitable form having aspect ratio greater than 1 may also be used. The terms particles, rod shaped particles and nanoparticles have been used to describe the nanoparticles of the present specification.

The nanoparticles 1 are multi-component particles. The surface chemistry of the nanoparticles 1 is controlled as required during formation. Further the rod shaped nanoparticles 1 have two physical dimensions which can be controlled and varied during manufacture, namely diameter and length. FIG. 19A shows a template deposition method for producing rod shaped particles 1. FIG. 19B shows an overview of the surface chemistry stages and FIG. 19C shows a schematic of an assay. The dimensions of the rod shaped nanoparticles 1 may be controlled by template deposition methods for example by control of both the reaction time and the template used. The template may comprise a membrane having regular cylindrical pores. An exemplary template may have pores having an average diameter of 250 nm, and this dimension ultimately controls one dimension— the diameter of the growing particle. The length of rod shaped particles 1 may be determined by the total charge passed during the course of the electro-deposition. The material within the rod can be controlled by varying the solution and potential under which the reaction takes place. The rod shaped nanoparticles 1 of FIG. 18 and FIG. 19 comprise Au and further comprise a segment 6 defining a capture site for capture probe 2. The locations and forms of the segment 6 and the capture probe 2 on the surface of the rod shaped particle 1 can accordingly be controlled and varied during manufacture. The control of the location and form of the capture probe 2 provides the necessary control of the manner in which the rod shaped particles 1 aggregate with an analyte and resulting control of the form of the aggregates. In the exemplary embodiment the segment 6 comprises a Ni segment. The Ni segment 6 is here modified with a His-tagged peptide, and the capture probe 2 for the analyte is then attached to the surface.

Referring to FIG. 19B, an arrangement is shown in which capture probe 2 is located at one end of the rod shaped particles 1, and the particles are configured to aggregate with an analyte oriented end to end resulting in complex 4 of increased length. In an alternative as shown in FIG. 18A the capture probe 2 is located between the ends of the rod 1 and spaced apart from the ends of the rod. In this case the particles 1 will not aggregate end to end but rather are configured to aggregate oriented side by side resulting in a complex 4 of increased size or width. Thus rod shaped particles 1 of the same size and form may be used to form aggregates of different shape and size.

The provision of the Ni segment 6 makes handling the rods much easier, during any surface chemistry modifications and subsequent wash stages the rods can be separated from solution using a simple hand held magnet as opposed to centrifugation. The Ni segment provides a loci for the capture probe for the analyte. This results in a "sticky" Ni segment that captures the analyte and acts as the centre for aggregation. It will be appreciated that while in the exemplary arrangement according to the specification Ni is used other suitable components could be included or used in place of the Ni. The nanoparticle 1 is a multi-component particle and additional components within a rod 1 can be selectively altered using specific chemistries. In the example described, the nanoparticles comprise Au and a Ni segment which is modified with a His-tagged peptide, it is known that the His tagged peptides will only attach to the Ni surface and not the Au, having first modified the Ni with the peptide the capture probe for the analyte can then be attached to the surface. Other peptides are known to attach to metals such as Co, Fe, Au, Ag, Pd, and Pt and could easily be incorporated into the rods 1 instead of or alongside the Ni segment. The rod shaped nanoparticles 1 may further be modified to incorporate additional required physical properties such as an optical or magnetic characteristic, by controlling the materials the rods are composed of. The optical or magnetic properties may be configured for detection.

The arrangement of the present specification and the rod shaped nanoparticles 1 provides for multiplex detection in a number of alternatives. While assays with spherical shaped beads where only the diameter can be varied for multiplexing, the rod shaped nanoparticles 1 have two physical dimensions which can be changed, diameter and length. Thus rod shaped nanoparticles 1 of different aspect ratios can be assigned to capture different and the frequency of their aggregates counted using a suitable detection system. Additionally the rod shaped nanoparticles 1 are multicomponent particles and it is possible to control the location of the capture probe in the rods surface and to direct the shape of the aggregation of the particles. The different forms of the aggregates of particles 1 are detectable and distinguishable. Detection of analyte 3 is achieved using a suitable detection system namely a system which can distinguish and count the different types of particle aggregates based on different shape and/or size.

Referring to FIG. 20 a detection system 30 comprising a nanopore is shown. In brief the system comprises a pore 31 of known dimensions. Further for example, a tunable nanopore system may be used. The detection system 30 is not described herein in detail. In brief, the system 30 comprises a pore 31 comprising a membrane 32. In the case of a tunable nanopore system the membrane may be stretched in a controlled and reversible manner to change the pore geometry as required. The pore is filled with a conducting media and a potential is applied between electrodes on either side of the opening to establish a current flow through the pore known as the baseline current ip which is proportional to applied voltage and electrolyte conductivity. The nanopore system 30 is used to monitor the behavior of the nanoparticles 1 as they move across the membrane pore opening 31, illustrated in FIG. 20A as having width d. The sample is placed into the upper fluid cell 33, and the particles move down through the pore under the influence of gravity into the lower fluid cell 34. During operation a current change $\Delta ip$ is registered when a particle moves through the pore causing a blockade event to occur. The volume the particle obstructs as it traverses the pore is related to peak height. Based on the proportionality between $\Delta ip$ and particle volume, measurement of the % change in $\Delta ip$ is used to provide an indication of particle size. The full width half maximum, FWHM indicative of duration time or time taken particle traversing the pore is also measured. The FWHM measurements for rod shaped particles are fundamentally different to those for example for spherical particles. The form of the rod shaped particles leads to an increase in dwell time within the pore attributable to the rod shaped particles moving through the pore in an orientated manner. A measurement of the FWHM is used to provide an indication of particle length.

A method is provided for detecting analytes in a sample. The method comprises providing nanoparticles 1 comprising a capture probe 2 for capturing the analyte 3, wherein the capture probe 2 is configured to act as a centre for controlled aggregation of nanoparticles 1 with the analyte to form aggregated particles of particular shape and/or size upon addition to the sample.

A nanopore system 30 is used to monitor the nanoparticles 1 passing therethrough. Blockade events indicated by % change in $\Delta ip$ and the duration or dwell time, FWHM, are monitored and measured. The % change in $\Delta ip$ is used to indicate particle volume and the FWHM is used to indicate particle length. The nanopore system is accordingly used to detect the presence of aggregates of different form. A count of the aggregates passing through the system is also maintained.

While a suitable detection system as described above comprises nanopore system, it will be appreciated that suitable alternative systems may also be used. For example, a tunable pore in which the dimensions of the pore may be varied may be used. Alternatively a detector device having different fixed pores may be used. It will be appreciated from the foregoing description that a suitable detector is a detector which may be configured to detect the different aggregates and to distinguish the different aggregates/different shapes and/or sizes.

The method may be applied to the multiplex detection of two or more analytes. According to a first approach, a method of detection of two different analytes is based on detection of complexes of different shape and size formed by nanoparticles 1 of the same size and form. In this case nanoparticles 1 of the same size and form are provided, each having a different capture probe 2 configured for the capture of different analytes 3. The capture probes 2 are configured to provide for the controlled aggregation of the nanoparticles by the location of the capture probe on the surface of the particle. The capture probe 2 of the nanoparticle 1 of the first type may be located at the end of the nanoparticle such that the nanoparticles 1 of the first type will aggregate end to end with the analyte resulting in an aggregate of increased length. The capture probe 2 of the nanoparticle 1 of the second type may be located between the ends of the nanoparticle such that the nanoparticles 1 of the second type will aggregate side by side with the analyte resulting in an aggregate of increased width. The nanoparticles of the first and second type are added to the sample. The sample is monitored using the nanopore system. The presence of rod shaped nanoparticles 1 of type 1 are configured aggregate end-on-end with an analyte (Type 1, FIG. 18B), is indicated by a simultaneous increase in $\Delta i_p$ and FWHM. The presence of rod shaped nanoparticles 1 of type 2 which are configured to aggregate in a side-on configuration with analyte (type 2, FIG. 18A), is indicated by a change in $\Delta i_p$ in the monitored signal.

In an alternative, the detection of different analytes may be based on detection of rod shaped particles 1 of first and second type having different aspect ratios each assigned to capture a different analyte. For example, rod shaped particles 1 of different length may be used each having capture probes 2 for different analytes. The rod shaped particles 1 may further be configured to aggregate end to end. Thus detection may be based on detection of complexes of different lengths. In the example 1 described in further detail below rod shaped particles 1 having lengths of the order of 2 microns and 5 microns respectively are used. The presence of aggregates of different length is indicated based on the simultaneous changes in $\Delta i_p$ and FWHM signals measured, indicative of increased volume and length. A nanopore detection system or a tunable nanopore detection system may be used.

Figures 21A, 21B, 21C, 21D:
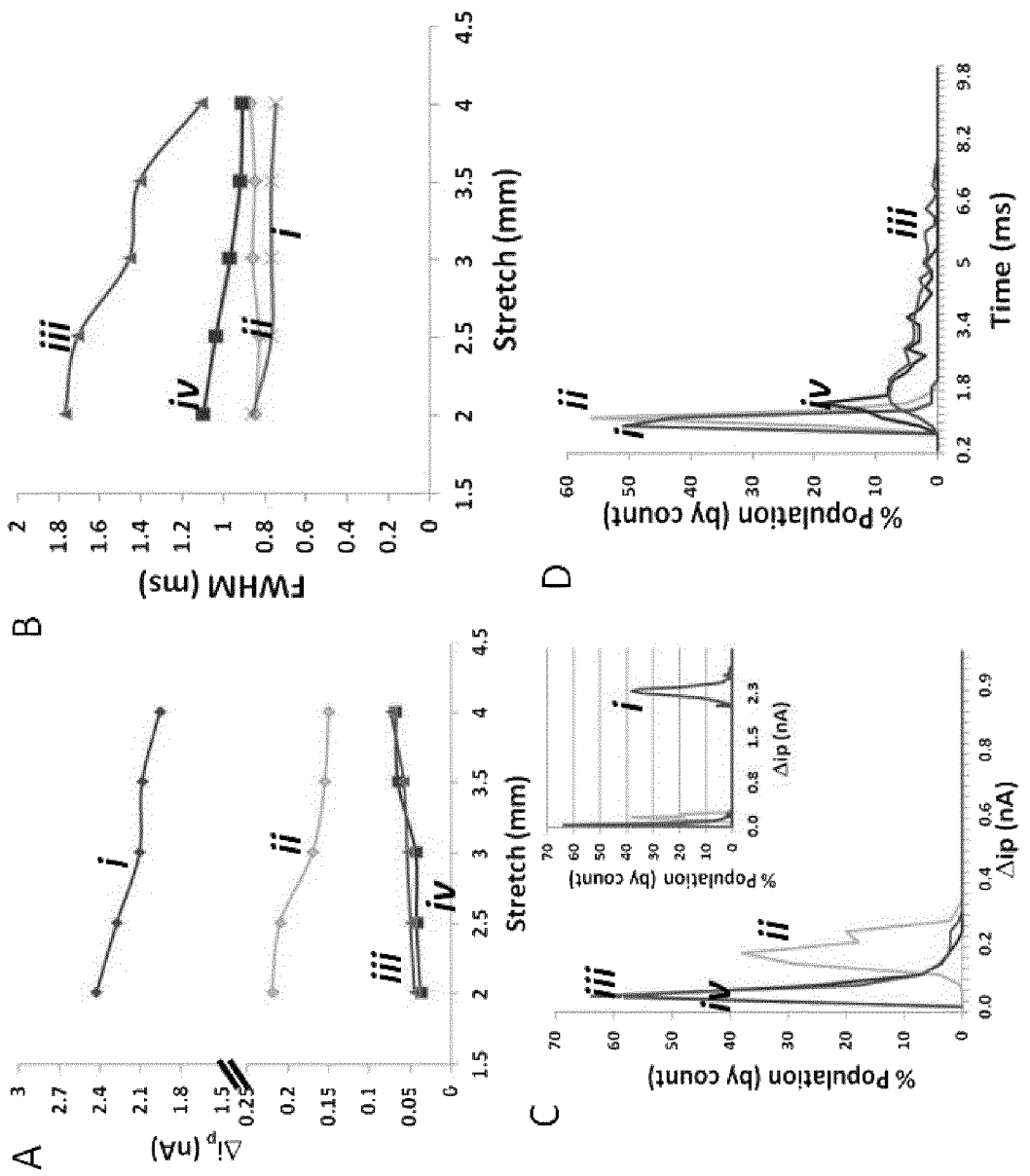
Figures 22A, 22B:
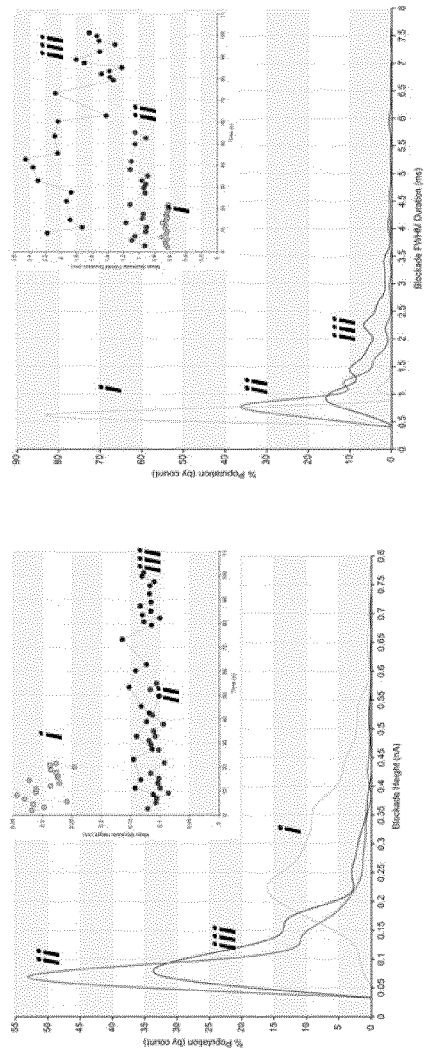

Referring to FIGS. 21, 22 and 23 the use of a nanopore system to detect analytes using rod shaped particles and a method according to the present specification is further described. Firstly the signal from rod shaped particles 1 as they traverse the pore was characterized, the $\Delta i_p$ is proportional to the volume/size of the particle, and that the rod length was monitored via the FWHM. By utilizing the two clear signals from rod shaped particles 1 an agglutination assay was designed, two capture probes 2 were chosen to demonstrate the assay format. The first was the model biotin-avidin system, the second capture probe 2 chosen was a DNA aptamer. The aptamer chosen here was the 35mer sequence which binds to the protein platelet derived growth factor, PDGF-BB, with a $K_d$~0.1 nM. Template deposition allows for nanoparticles to be produced with dimensions that are controlled by both the reaction time, as well as the template itself. The pores within the $Al_2O_3$ membrane have an average diameter of circa 300 nm, and determined the diameter of the growing particle. The length of the rod was determined by the total charge passed during the course of the electrodeposition. The composition of material within the multi-component rod 1 was controlled by varying the plating solution as well as the potential under which the reaction takes place. In the example arrangement of FIGS. 21 to 23 a tunable pore detection system having the ability to stretch the pore during use, as described above was used to detect aggregates of particles 1 with analytes. The measurements (FIG. 21) record the $\Delta i_p$ and FWHM as the pore size was increased. Two sizes of spheres, 0.95 µm and 2 µm in diameter, and rods composed of Au, 2.1 µm and 4.7 µm in length were used. In FIG. 21A the $\Delta i_p$ can be seen to decrease for the spherical particles as the pore size is increased. In contrast the $\Delta ip$ for the rods increased with stretch. It is clear from FIG. 21B that across all stretches the two rod shaped particles produce a FWHM value much larger than the spherical beads. The 4.7 µm rods record the largest FWHM values which implies the longest translocation time. A simple control assay to determine the sensitivity of the tunable pore system to solutions that contained mixtures of the 2.1 µm and 4.7 µm Au rods was performed.

Referring to FIG. 22A Height (nA) versus % population. Insert—average size (y axis) over the course of the experiment in seconds (x axis). FIG. 5 FWHM (ms) vents % population; i=1 micron sphere; ii=4.7 micron long rod; and iii=2 micron long rod.

Referring to FIG. 23, initially a solution containing 2.1 µm rods was analyzed, the molar fraction of the 4.7 µm rod was then increased from 0 to 10, 25, 50, 75, 90 and 100% the modal $\Delta i_p$ (FIG. 23A) and FWHM (FIG. 23B), values are plotted as % change from the initial 2.1 µm rod solution. The FWHM values increase with increasing fraction of 4.7 µm rods.

Example Avidin—Biotin Assay.

Figure 24:
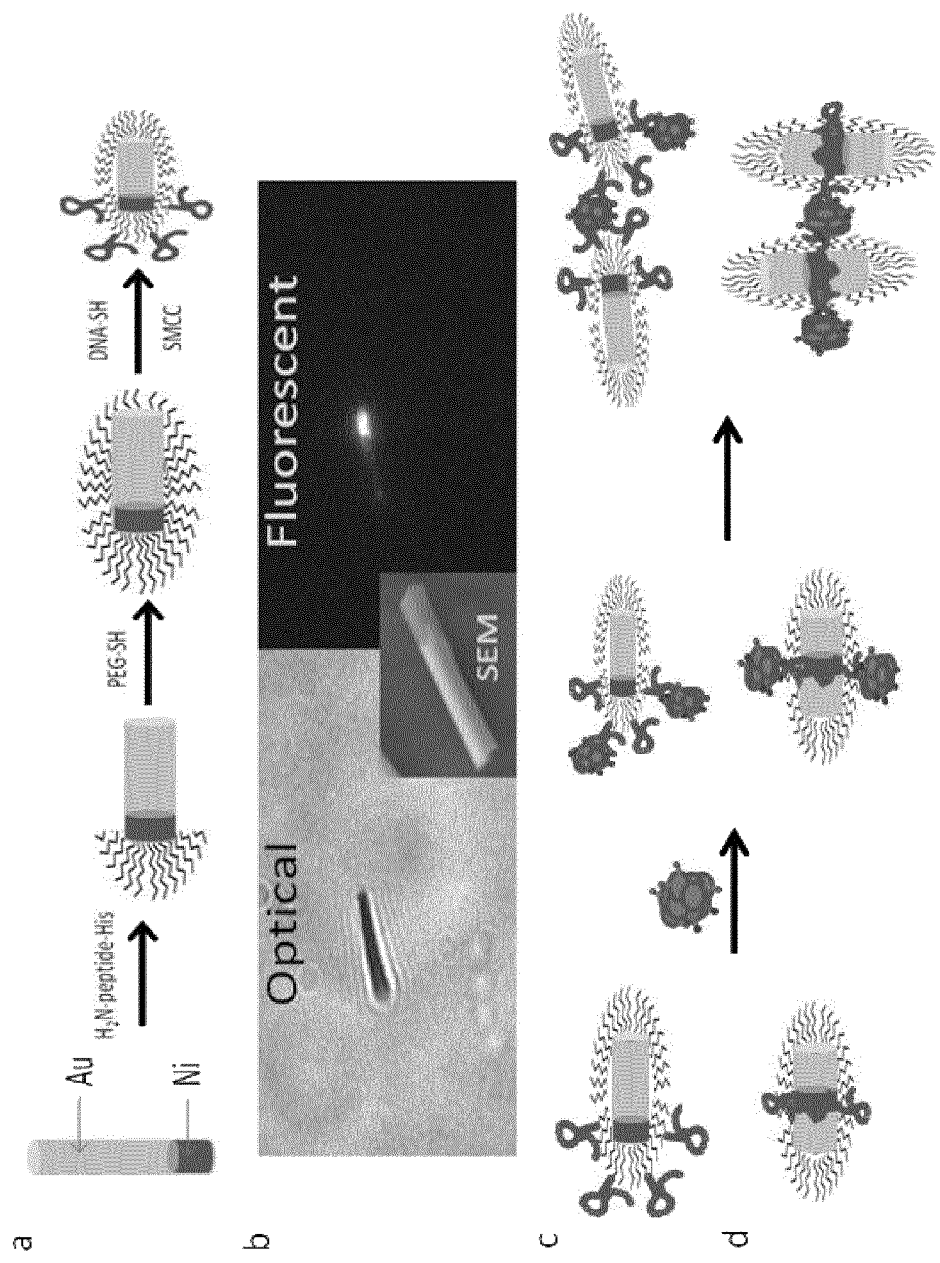

A further example assay according to the present specification is described with reference to FIG. 24A schematic of the rod shaped nanoparticles 1 used for the agglutination assays are shown in FIG. 24. By controlling the orientation in which the rods are made to aggregate, rods 1 of similar aspect ratios are used to produce alternate signal responses in the presence of a target analyte 3, thus making agglutinations assays easier to multiplex with the rod shaped particles 1 and a tunable pore system. For rods aggregated end-on-end, (FIG. 24C), a simultaneous increase in $\Delta ip$ and FWHM is expected, where rods are made to aggregate in a side-on configuration (FIG. 7D) only a change in $\Delta i_p$ is expected. The capture probes were conjugated to the Ni surface using a His-modified peptide. The peptides contained a 6× Histidine tag on one end and 4 residual amine groups on the opposite, for conjugation to the capture probe of interest. Two different capture probes were conjugated to the rods the first was an avidin protein, these particles were used as a control assay to monitor the changes in behavior in the presence of a biotinylated protein target. To first confirm the surface chemistry performed as shown in the schematic, the Ni modified avidin particles were incubated for 5 mins with a solution of biotinylated-FITC. A localized fluorescent signal confirmed its success, FIG. 24B.

The effect of this was to cause the slow aggregation of the particles if they were left in solution without sonication for periods longer than 20 minutes. FIG. 24A shown the % change in $\Delta i_p$ and FWHM for 1 µm rods, end functionalized with Ni, in a buffered solution. The solution was placed on a rotating wheel and sampled at 5 min intervals. A slight increase in $\Delta i_p$ and FWHM was measured. It was clear that the Ni causes the nonspecific aggregation of the particles at short reaction times, however it should occur at a level low enough not to be the dominant signal during the aggregation in the presence of an analyte. A 10 min assay time was chosen based upon the calculated mutual diffusion coefficient of $5.6 \times 10^{-8}$ cm$^2$s$^{-1}$ for rods 1 µm in length and 150 nm in radius, given a concentration of particles circa 300-500 fM, these conditions should be sufficient time for the assay to be completed, given that the rate determining step of the diffusion of the analyte to the rod. In each assay a blank was run to allow the % change for FWHM and $\Delta ip$ to be calculated. FIG. 24B shows the change in $\Delta ip$ and FWHM for an assay using end functionalized rods, where the Ni segment was conjugated to avidin. The rods were first sonicated, an aliquot was then drawn from the stock solution, to this was added an equal volume of analyte solution, the final dilutions and concentrations of the particles are plotted in FIG. 24. A similar protocol was used for the rods containing a Ni segment in the middle, results from the side-on assay are shown in FIG. 24C.

PDGF Assay.

An end-on-end assay format for the detection of PDGF is described with reference to FIG. 25. It is known that that the aptamer binds to the protein in a 2:1 ratio. As in the case of the avidin example above, an increase in both the $\Delta ip$ and FWHM was shown FIG. 25D, a control assay for the same rods using a different protein (BSA) produced small changes in FWHM and $\Delta i_p$ (FIG. 25D circled data points), demonstrating that the aggregation was not nonspecific. Despite the 2.1 μm rod having a similar dimension as the 2 μm diameter sphere, the rod particles produce a FWHM significantly higher (FIG. 21B). As the rod length is increased the FWHM values also increase and is attributed to the fact that the rods pass through the pore vertically.

Example

Agglutination assay. Rods were synthesized containing a Ni segment, to which was first conjugated the avidin protein. Increasing the concentration of biotinylated-BSA in the solution causes two trends in the recorded values to be noted (FIG. 25B). First, both the $\Delta i_p$ and FWHM values rise, the increase in signal continues to a concentration of 250 fM, before the number of binding sites on the particles start to become saturated a hook effect is observed. Second, the change in the FWHM is the dominant signal, as the rods aggregate forming longer rods. The increase in rod length, as demonstrated within the control assay (FIG. 4B) results in changes in FWHM that are much larger then $\Delta ip$. Rods from the same synthesis batch were also exposed to a non-biotinylated protein target, a small percentage change in both $\Delta i_p$, and FWHM was observed, (FIG. 25B (dashed lines)). The results from the side-on assay are shown in FIG. 25C, an increase in analyte concentration causes a clear increase in $\Delta i_p$, where as the FWHM does not change significantly. This side-on aggregation has the effect of forming rods with larger diameters but a constant FWHM. Similar behaviors were recorded for the PDGF assay using the end-on-end format. The sensitivity is as low as 10 fM, using the same capture probe, however the percentage change in both the FWHM and $\Delta ip$ is much lower than the example using avidin—biotin.

The present specification accordingly provides an improved system and method for detection of analytes. Rod shaped nanoparticles according to the specification are provided. The nanoparticles are configured to aggregate in a controlled manner in the presence of an analyte. The form of the aggregates is detectable and distinguishable. Analytes are detected using a suitable detection system, for example in this case a tunable nanopore system is used. Unlike detection formats such as light scattering of colorimetric assay where the physical properties of the entire population of particles are measured simultaneously, with the methods described each of the particles/aggregates is measured independently as they traverse the pore, building up readings that represent the population. Accordingly the method is advantageously accurate and sensitive.

The movement of rod shaped particles through a pore detection system has been shown. It has been shown that as the rods traverse the pores the $\Delta i_p$ is sensitive to the volume of the particle and the FWHM values provide an indication of the length, as by increasing the length of the rod/aggregate a much slower translocation time is recorded. An agglutination assay is accordingly provided where by controlling the orientation in which the rods aggregation either the $\Delta i_p$ or the FWHM can be used as the indicator for the detection an analyte.

The present specification further provides multi-component rods composed for example of Au and having a segment that can be selectively activated with a capture probe of interest, and as such the segment can be configured to act as a locus for aggregation. The control over the signal created when the rods shaped particles aggregate advantageously makes agglutination assays much easier to multiplex. Using this dual signal, rather than creating a new aspect ratio rod for each analyte, similar sized rods can be used for two different targets simplifying particles synthesis. Further the provision of the nanoparticles 1 according to the present specification being configured to aggregate to form complexes of different shape and/or size makes multiplex detection much easier and far simpler. For example, a nanopore system or a tunable nanopore system may be used for multiplexed detection while optimised for one size of particles.

The ability to control the shape has not been shown using spherical beads and is a highly advantageous property of the rod shaped particles of the present specification. Further, a suitable detection system for example a tunable nanopore system described above can advantageously distinguish also between rods and spheres. The length of the rod can be detected using FWHM. Aggregation of rods leads to an increase in size which is detected using the detector. Controlled aggregation of the rods can also lead to an increase in FWHM. The rods of the specification advantageously allow for a more sensitive assay and also for multiplexed detection.

The words comprises/comprising when used in this specification are to specify the presence of stated features, integers, steps or components but does not preclude the presence or addition of one or more other features, integers, steps, components or groups thereof.

The invention claimed is:

1. A method of aggregating a plurality of beads for subsequent analysis comprising:
providing a container, defining a reaction chamber, with a sample solution and a plurality of beads in the sample solution, wherein the plurality of beads comprises magnetic beads of a first type comprising a capture probe for binding with a first analyte and magnetic beads of a second type comprising a capture probe for binding with a second analyte, the magnetic beads of the first type and the magnetic beads of the second type being uniform in their physical properties of magnetization, color and size and comprising carboxyl coated particles modified with a protective polyethylene glycol (PEG) layer;
incubating the beads with the first analyte and the second analyte;
applying a magnetic field of a first orientation to the reaction chamber containing the sample solution;
allowing the beads to migrate to and collect on a side surface of the container in the presence of a magnetic field of a first orientation until the beads have separated from the sample solution;
subsequent to collecting the beads on the side surface of the container, replacing the sample solution with a new second solution in the container and stirring the second solution to suspend the beads;

reapplying the magnetic field of the first orientation to the second solution and the beads and collecting the beads on the side surface of the container for a second time;

exposing the beads to a magnetic field of a second orientation to allow formation of aggregates of the beads and the analytes by increasing the bead to bead interactions, comprising moving the beads relative to the magnetic field of the second orientation, wherein the container and the beads collected on the side of the container is rotated 90 degrees while maintaining the magnetic field of the second orientation such that the beads roll to the side of the container and settle on the side of the container as aggregates comprising monomer or dimer or trimer or tetramer aggregates; and collecting the aggregates, wherein aggregates of the first type of magnetic beads and the first analyte and aggregates of the second type of magnetic beads and the second analyte each have predefined physical properties detectable to enable characterization of the aggregates of the first type of magnetic beads and the aggregates of the second type of magnetic beads on a bead by bead basis using a detector to measure the physical properties of the aggregates to detect the first and second analytes.

2. The method of claim 1 wherein the beads are superparamagnetic beads.

3. The method of claim 1 wherein the magnetic beads further comprise a protein coating.

4. The method of claim 3 wherein the protein coated magnetic beads are coupled to a biotinylated nucleic acid probe.

5. The method of claim 3 wherein the protein is streptavidin.

6. The method of claim 1 wherein the aggregation of magnetic beads to form aggregates is controllable by controlling bead concentration.

7. The method of claim 1 wherein the aggregation of magnetic beads to form aggregates is controllable by controlling binding capacity.

8. The method of claim 1 wherein the magnetic beads are reacted with the sample for a reaction time and wherein aggregation of magnetic beads to form aggregates is controllable by controlling reaction time.

9. The method of claim 8 wherein an increased reaction time provides an increase in the aggregation rate.

10. The method of claim 1 further comprising the step of applying a magnetic force to provide the magnetic field for aggregating the magnetic beads wherein the aggregation of magnetic beads to form aggregates is controllable by controlling application of magnetic force.

11. The method of claim 1 wherein the PEG comprises a mixed butyloxycarbonyl (BOC) terminated PEG functionality.

12. The method of claim 11 wherein a streptavidin protein is conjugated onto the bead surface.

13. The method of claim 1 wherein the method is a reagent-free method.

14. A method of aggregating a plurality of beads for subsequent analysis comprising:

providing a container, defining a reaction chamber, with a sample solution and a plurality of beads, wherein the plurality of beads comprises magnetic beads of a first type comprising a capture probe for binding with a first analyte and magnetic beads of a second type comprising a capture probe for binding with a second analyte, the magnetic beads of the first type and the magnetic beads of the second type being uniform in their physical properties of magnetization, color and size and comprising carboxyl coated particles modified with a protective polyethylene glycol (PEG) layer;

incubating the beads with the analytes;

applying a magnetic field of a first orientation to the reaction chamber containing the sample solution and the beads;

allowing the beads to migrate to and collect on a side surface of the container, wherein the sample solution is left in the presence of a magnetic field of a first orientation until the beads have separated from the solution;

subsequent to collecting the beads on the side surface of the container, replacing the sample solution with a second solution and stirring the second solution with the collected beads;

re-applying the magnetic field of the first orientation, separating the beads from the second solution, and collecting the beads on the side surface of the container for a second time;

exposing the beads to a magnetic field of a second orientation to increase the bead interactions and increase the number of aggregates comprising the beads and the analytes, comprising maintaining the beads stationary while varying the direction of the magnetic field of the second orientation such that the beads roll to the side of the container and settle on the side of the container forming aggregates comprising monomer or dimer or trimer or tetramer aggregates; and collecting the aggregates, wherein aggregates of the first type of magnetic beads and the first analyte and aggregates of the second type of magnetic beads and the second analyte each have predefined physical properties detectable to enable characterization of the aggregates of the first type of magnetic beads and the aggregates of the second type of magnetic beads on a bead by bead basis using a detector to measure the physical properties of the aggregates to detect the first and second analytes.

15. The method of claim 14 wherein the method is a reagent-free method.

* * * * *